(12) United States Patent
Raymond et al.

(10) Patent No.: US 10,279,189 B2
(45) Date of Patent: May 7, 2019

(54) WEARABLE MULTIPHASIC CARDIOVERTER DEFIBRILLATOR SYSTEM AND METHOD

(71) Applicant: CardioThrive, Inc., Concord, CA (US)

(72) Inventors: Douglas M. Raymond, Livermore, CA (US); Peter D. Gray, Vallejo, CA (US); Walter T. Savage, Concord, CA (US); Shelley J. Savage, Concord, CA (US)

(73) Assignee: CardioThrive, Inc., Concord, CA (US)

( * ) Notice: Subject to any disclaimer, the term of this patent is extended or adjusted under 35 U.S.C. 154(b) by 0 days.

(21) Appl. No.: 14/303,543

(22) Filed: Jun. 12, 2014

(65) Prior Publication Data

US 2014/0371806 A1 Dec. 18, 2014

Related U.S. Application Data

(60) Provisional application No. 61/835,459, filed on Jun. 14, 2013.

(51) Int. Cl.
*A61N 1/39* (2006.01)
*A61N 1/04* (2006.01)

(52) U.S. Cl.
CPC ........... *A61N 1/3968* (2013.01); *A61N 1/046* (2013.01); *A61N 1/0484* (2013.01); *A61N 1/3906* (2013.01)

(58) Field of Classification Search
CPC .... A61N 1/3968; A61N 1/0484; A61N 1/046; A61N 1/3906
See application file for complete search history.

(56) References Cited

U.S. PATENT DOCUMENTS

| | | |
|---|---|---|
| 3,782,389 A | 1/1974 | Bell |
| 4,441,498 A | 4/1984 | Nordling |
| 5,199,429 A | 4/1993 | Kroll et al. |
| 5,240,995 A | 8/1993 | Gyory et al. |
| 5,290,585 A | 3/1994 | Elton |
| 5,338,490 A | 8/1994 | Dietz |
| 5,362,420 A | 11/1994 | Itoh |
| 5,402,884 A | 4/1995 | Gilman et al. |
| 5,489,624 A | 2/1996 | Kantner |
| 5,536,768 A | 7/1996 | Kantner |
| 5,573,668 A | 11/1996 | Grosh |
| 5,643,252 A | 7/1997 | Waner et al. |
| 5,658,316 A | 8/1997 | Lamond et al. |
| 5,660,178 A | 8/1997 | Kantner |
| 5,733,310 A | 3/1998 | Lopin et al. |
| 5,800,685 A | 9/1998 | Perrault |
| 5,871,505 A | 2/1999 | Adams |

(Continued)

FOREIGN PATENT DOCUMENTS

| | | |
|---|---|---|
| DE | 10 2006 025864 | 12/2007 |
| EP | 1 530 983 | 5/2005 |

(Continued)

OTHER PUBLICATIONS

PCT International Search Report of PCT/US2012/065712, dated Mar. 29, 2013 (2 pages).

(Continued)

*Primary Examiner* — Rex R Holmes
(74) *Attorney, Agent, or Firm* — DLA Piper LLP (US)

(57) ABSTRACT

A wearable, multiphasic cardioverter defibrillator system and method are provided.

23 Claims, 23 Drawing Sheets

(56) References Cited

U.S. PATENT DOCUMENTS

| | | |
|---|---|---|
| 5,987,354 A | 11/1999 | Cooper |
| 6,004,312 A | 12/1999 | Finneran et al. |
| 6,006,131 A | 12/1999 | Cooper et al. |
| 6,056,738 A | 5/2000 | Marchitto et al. |
| 6,141,584 A | 10/2000 | Rockwell et al. |
| 6,197,324 B1 | 3/2001 | Crittenden |
| 6,251,100 B1 | 6/2001 | Flock et al. |
| 6,256,533 B1 | 7/2001 | Yuzhakov et al. |
| 6,266,563 B1 | 7/2001 | Kenknight et al. |
| 6,315,722 B1 | 11/2001 | Yaegashi |
| 6,329,488 B1 | 12/2001 | Terry |
| 6,379,324 B1 | 4/2002 | Gartstein et al. |
| 6,477,413 B1 | 11/2002 | Sullivan et al. |
| 6,576,712 B2 | 6/2003 | Feldstein |
| 6,596,401 B1 | 7/2003 | Terry |
| 6,597,948 B1 | 7/2003 | Rockwell et al. |
| 6,611,707 B1 | 8/2003 | Prausnitz |
| 6,690,959 B2 | 2/2004 | Thompson |
| 6,714,817 B2 | 3/2004 | Daynes et al. |
| 6,797,276 B1 | 9/2004 | Glenn |
| 6,803,420 B2 | 10/2004 | Cleary |
| 6,908,453 B2 | 6/2005 | Fleming |
| 6,908,681 B2 | 6/2005 | Terry |
| 6,931,277 B1 | 8/2005 | Yuzhakov |
| 7,072,712 B2 | 7/2006 | Kroll et al. |
| 7,108,681 B2 | 9/2006 | Gartstein |
| 7,215,991 B2 | 5/2007 | Besson et al. |
| 7,226,439 B2 | 6/2007 | Prausnitz |
| 7,463,917 B2 | 12/2008 | Martinez |
| 7,645,263 B2 | 1/2010 | Angel et al. |
| 7,797,044 B2 | 9/2010 | Covey et al. |
| 8,024,037 B2 | 9/2011 | Kumar |
| 8,333,239 B2 | 12/2012 | Schneider et al. |
| 8,527,044 B2 | 9/2013 | Edwards et al. |
| 8,558,499 B2 | 10/2013 | Ozaki et al. |
| 8,615,295 B2 | 12/2013 | Savage et al. |
| 8,781,576 B2 | 7/2014 | Savage et al. |
| 9,089,718 B2 | 7/2015 | Owen et al. |
| 9,101,778 B2 | 8/2015 | Savage et al. |
| 9,616,243 B2 | 4/2017 | Raymond et al. |
| 9,656,094 B2 | 5/2017 | Raymond et al. |
| 2001/0031992 A1 | 10/2001 | Fishler et al. |
| 2002/0016562 A1 | 2/2002 | Cormier et al. |
| 2002/0045907 A1 | 4/2002 | Sherman et al. |
| 2002/0082644 A1 | 6/2002 | Picardo et al. |
| 2003/0017743 A1 | 1/2003 | Picardo et al. |
| 2003/0055460 A1 | 3/2003 | Owen et al. |
| 2003/0088279 A1 | 5/2003 | Rissmann et al. |
| 2003/0125771 A1 | 7/2003 | Garrett et al. |
| 2003/0167075 A1 | 9/2003 | Fincke |
| 2003/0197487 A1 | 10/2003 | Tamura et al. |
| 2004/0105834 A1 | 6/2004 | Singh et al. |
| 2004/0143297 A1 | 7/2004 | Ramsey, III |
| 2004/0166147 A1 | 8/2004 | Lundy et al. |
| 2004/0247655 A1 | 12/2004 | Asmus |
| 2005/0107713 A1 | 5/2005 | Van Herk |
| 2005/0107833 A1* | 5/2005 | Freeman .............. A61N 1/3918 607/5 |
| 2005/0123565 A1 | 6/2005 | Subramony |
| 2006/0136000 A1 | 6/2006 | Bowers |
| 2006/0142806 A1 | 6/2006 | Katzman et al. |
| 2006/0173493 A1 | 8/2006 | Armstrong et al. |
| 2006/0206152 A1 | 9/2006 | Covey et al. |
| 2007/0016268 A1 | 1/2007 | Carter et al. |
| 2007/0078376 A1 | 4/2007 | Smith |
| 2007/0135729 A1 | 6/2007 | Ollmar et al. |
| 2007/0143297 A1 | 6/2007 | Recio et al. |
| 2007/0150008 A1 | 6/2007 | Jones et al. |
| 2007/0191901 A1 | 8/2007 | Schecter |
| 2008/0082153 A1 | 4/2008 | Gadsby et al. |
| 2008/0097546 A1 | 4/2008 | Powers et al. |
| 2008/0154110 A1 | 6/2008 | Burnes et al. |
| 2008/0154178 A1 | 6/2008 | Carter et al. |
| 2008/0177342 A1* | 7/2008 | Snyder ............... A61N 1/3906 607/8 |
| 2008/0312579 A1 | 12/2008 | Chang et al. |
| 2008/0312709 A1 | 12/2008 | Volpe et al. |
| 2009/0005827 A1 | 1/2009 | Weintraub et al. |
| 2009/0076366 A1 | 3/2009 | Palti |
| 2009/0210022 A1 | 8/2009 | Powers |
| 2009/0318988 A1 | 12/2009 | Powers |
| 2009/0326400 A1 | 12/2009 | Huldt |
| 2010/0063559 A1 | 3/2010 | McIntyre et al. |
| 2010/0160712 A1 | 6/2010 | Burnett et al. |
| 2010/0191141 A1 | 7/2010 | Aberg |
| 2010/0241181 A1 | 9/2010 | Savage et al. |
| 2010/0249860 A1 | 9/2010 | Shuros et al. |
| 2011/0028859 A1 | 2/2011 | Chian |
| 2011/0071611 A1 | 3/2011 | Khuon et al. |
| 2011/0208029 A1 | 8/2011 | Joucla et al. |
| 2011/0237922 A1 | 9/2011 | Parker, III et al. |
| 2011/0288604 A1 | 11/2011 | Kaib et al. |
| 2011/0301683 A1 | 12/2011 | Axelgaard |
| 2012/0101396 A1 | 4/2012 | Solosko et al. |
| 2012/0112903 A1 | 5/2012 | Kalb |
| 2012/0136233 A1 | 5/2012 | Yamashita |
| 2012/0158075 A1 | 6/2012 | Kaib et al. |
| 2012/0158078 A1 | 6/2012 | Moulder et al. |
| 2012/0203297 A1 | 8/2012 | Efimov et al. |
| 2012/0259382 A1 | 10/2012 | Trier |
| 2013/0018251 A1 | 1/2013 | Caprio et al. |
| 2013/0144365 A1 | 6/2013 | Kipke et al. |
| 2014/0005736 A1* | 1/2014 | Geheb ................ A61N 1/3987 607/7 |
| 2014/0039593 A1 | 2/2014 | Savage et al. |
| 2014/0039594 A1 | 2/2014 | Savage et al. |
| 2014/0221766 A1 | 8/2014 | Kinast |
| 2014/0276183 A1 | 9/2014 | Badower |
| 2014/0277226 A1* | 9/2014 | Poore ................ A61N 1/0484 607/7 |
| 2014/0317914 A1 | 10/2014 | Shaker |
| 2014/0371566 A1 | 12/2014 | Raymond et al. |
| 2014/0371567 A1 | 12/2014 | Raymond et al. |
| 2014/0371805 A1 | 12/2014 | Raymond et al. |
| 2014/0371806 A1 | 12/2014 | Raymond et al. |
| 2015/0297104 A1 | 10/2015 | Chen |
| 2015/0327781 A1 | 11/2015 | Hernandez-Silveira |
| 2016/0206893 A1 | 7/2016 | Raymond et al. |
| 2016/0213933 A1 | 7/2016 | Raymond et al. |
| 2016/0213938 A1 | 7/2016 | Raymond et al. |
| 2016/0296177 A1 | 10/2016 | Gray et al. |
| 2016/0361533 A1 | 12/2016 | Savage et al. |
| 2016/0361555 A1 | 12/2016 | Savage et al. |
| 2017/0252572 A1 | 9/2017 | Raymond et al. |
| 2018/0064948 A1 | 3/2018 | Raymond et al. |

FOREIGN PATENT DOCUMENTS

| | | |
|---|---|---|
| EP | 1 834 622 | 9/2007 |
| JP | S63-296771 | 12/1988 |
| JP | 2000-093526 | 4/2000 |
| JP | 2005-144164 | 6/2005 |
| JP | 2007-530124 | 11/2007 |
| JP | 2008-302254 | 12/2008 |
| JP | 2010-511438 | 4/2010 |
| JP | 2010-529897 | 9/2010 |
| JP | 2011-512227 | 4/2011 |
| JP | 2012-135457 | 7/2012 |
| JP | 2012-529954 | 11/2012 |
| WO | 03/020362 | 3/2003 |
| WO | WO2010/146492 | 12/2010 |
| WO | WO2010/151875 | 12/2010 |

OTHER PUBLICATIONS

PCT Written Opinion of PCT/US2012/065712, dated Mar. 29, 2013 (5 pages).
PCT International Preliminary Report on Patentability and Written Opinion of PCT/EP2007/009879; dated May 19, 2009 (7 pages).
PCT International Search Report of PCT/EP2007/009879; dated Apr. 29, 2008 (3 pages).
PCT International Preliminary Report on Patentability of PCT/US2010/027346 dated Sep. 20, 2011 (12 pages).

(56) References Cited

OTHER PUBLICATIONS

Extended European Search Report of EP 2408521 dated Jul. 10, 2012 (8 pages).
"Changes in the passive electrical properties of human stratum corneum due electroporation" dated Dec. 7, 1994. By U. Pliquett, R. Langer, and J. C. Weaver (11 pages).
"Electrical properties of the epidermal stratum corneum" dated Aug. 12, 1974. By T. Yamamoto and Y. Yamamoto (8 pages).
"Non-invasive bioimpedance of intact skin: mathematical modeling and experiments" dated May 2, 2010. By U. Birgersson, E. Birgersson, P. Aberg, I. Nicander, and S. Ollmar (19 pages).
"Polymer Microneedles for Controlled-Release Drug Delivery" dated Dec. 2, 2005. By J-H. Park, M. G. Allen, and M. R. Prausnitz (12 pages).
"Utilizing Characteristic Electrical Properties of the Epidermal Skin Layers to Detect Fake Fingers in Biometric Fingerprint Systems—A Pilot Study" dated Dec. 1, 2004. By O. G. Martinsen, S. Clausen, J. B. Nysaether, and S. Grimnes (4 pages).
"Lack of Pain Associated with Microfabricated Microneedles" dated Oct. 10, 2000. By S. Kaushik, A. H. Hord, D. D. Denson, D. V. McAlliser, S. Smitra, M. G. Allen, and M. R. Prausnitz (3 pages).
"Two Dimensional Metallic Microelectrode Arrays for Extracellular Stimulation and Recording of Neurons" dated 1993. By A. B. Frazier, D. P. O'Brien, and M. G. Allen (6 pages).
"Insertion of microneedles into skin: measurement and prediction of insertion force and needle facture force" dated Dec. 10, 2003. By S. P. Davis, B. J. Landis, Z. H. Adams, M. G. Allen, and M. R. Prausnitz (9 pages).
"Microneedle Insertion Force Reduction Using Vibratory Actuation" dated 2004. By M. Yang and J. D. Zahn (6 pages).
PCT International Search Report of PCT/US10/27346; dated Oct. 14, 2010 (4 pgs.).
PCT Written Opinion of the International Searching Authority of PCT/US10/27346; dated Oct. 14, 2010 (7 pgs.).
PCT International Preliminary Report on Patentability of PCT/US12/65712; dated Jun. 10, 2014 (6 pgs.).
PCT International Search Report of PCT/US14/42355; dated Nov. 3, 2010 (2 pgs.).
PCT Written Opinion of the International Searching Authority of PCT/US14/42355; dated Nov. 3, 2014 (6 pgs.).
PCT International Search Report of PCT/US14/42356; dated Nov. 3, 2010 (2 pgs.).
PCT Written Opinion of the International Searching Authority of PCT/US14/42356; dated Nov. 3, 2014 (6 pgs.).
PCT International Search Report of PCT/US14/42360; dated Nov. 4, 2010 (2 pgs.).
PCT Written Opinion of the International Searching Authority of PCT/US14/42360; dated Nov. 4, 2014 (4 pgs.).
PCT International Search Report of PCT/US14/42409; dated Nov. 4, 2010 (2 pgs.).
PCT Written Opinion of the International Searching Authority of PCT/US14/42409; dated Nov. 4, 2014 (4 pgs.).
Chinese First Office Action of CN 201080021650.4 (English and Chinese); dated Jul. 24, 2013 (19 pgs.).
Chinese Second Office Action of CN 201080021650.4 (English and Chinese); dated Jan. 16, 2014 (16 pgs.).
Chinese Third Office Action of CN 201080021650.4 (English and Chinese); dated Jun. 17, 2014 (8 Pages).
Japanese Notification of Reason for Rejection of JP 2012-500855 (English and Japanese); dated Feb. 17, 2014 (3 pgs.).
Yamanouchi, et al., *Optimal Small-Capacitor Biphasic Waveform for External Defibrillation; Influence of Phase-1 Tilt and Phase-2 Voltage*, Journal of the American Heart Association, Dec. 1, 1998, vol. 98, pp. 2487-2493 (8 pgs.).
CN 201080021650.4, First Office Action dated Jul. 24, 2013 (English and Chinese) (19 pgs.).

* cited by examiner

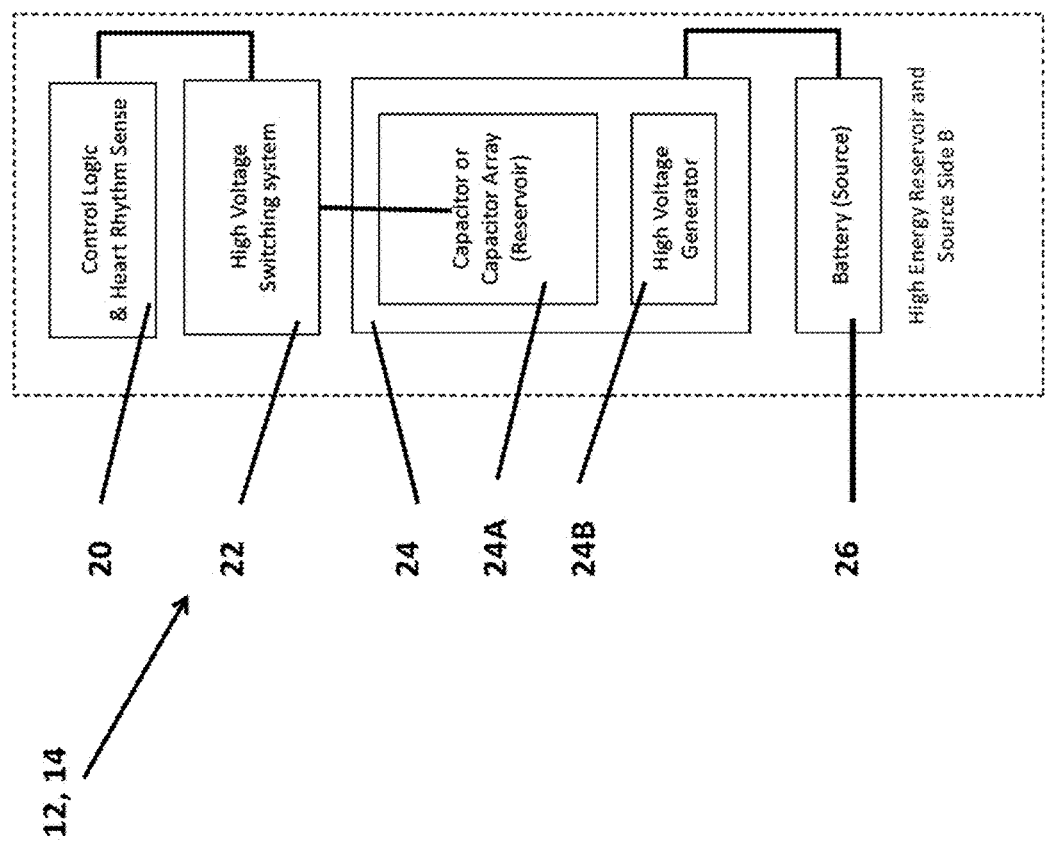

WEARABLE MULTIPHASIC CARDIOVERTER DEFIBRILLATOR SYSTEM AND METHOD

PRIORITY CLAIMS

This application claims priority to under 35 USC 120 and the benefit under 35 USC 119(e) to U.S. Provisional Patent Application Ser. No. 61/835,459, filed on Jun. 14, 2013 and titled "Wearable Multiphasic Cardioverter Defibrillator System And Method", the entirety of which is incorporated by reference herein.

FIELD

The disclosure relates generally to methods and arrangements relating to medical devices. More specifically, the disclosure relates to the systems and methods used in external defibrillators and in a preferred embodiment to wearable cardioverter defibrillators.

BACKGROUND

A primary task of the heart is to pump oxygenated, nutrient-rich blood throughout the body. Electrical impulses generated by a portion of the heart regulate the pumping cycle. When the electrical impulses follow a regular and consistent pattern, the heart functions normally and the pumping of blood is optimized. When the electrical impulses of the heart are disrupted (i.e., cardiac arrhythmia), this pattern of electrical impulses becomes chaotic or overly rapid, and a Sudden Cardiac Arrest may take place, which inhibits the circulation of blood. As a result, the brain and other critical organs are deprived of nutrients and oxygen. A person experiencing Sudden Cardiac Arrest may suddenly lose consciousness and die shortly thereafter if left untreated.

The most successful therapy for Sudden Cardiac Arrest is prompt and appropriate defibrillation. A defibrillator uses electrical shocks to restore the proper functioning of the heart. A crucial component of the success or failure of defibrillation, however, is time. Ideally, a victim should be defibrillated immediately upon suffering a Sudden Cardiac Arrest, as the victim's chances of survival dwindle rapidly for every minute without treatment.

There are a wide variety of defibrillators. For example, Implantable Cardioverter-Defibrillators (ICD) involve surgically implanting wire coils and a generator device within a person. ICDs are typically for people at high risk for a cardiac arrhythmia. When a cardiac arrhythmia is detected, a current is automatically passed through the heart of the user with little or no intervention by a third party.

Another, more common type of defibrillator is the automated external defibrillator (AED). Rather than being implanted, the AED is an external device used by a third party to resuscitate a person who has suffered from sudden cardiac arrest. FIG. 19 illustrates a conventional AED 1900, which includes a base unit 1902 and two pads 1904. Sometimes paddles with handles are used instead of the pads 1904. The pads 1904 are connected to the base unit 1902 using electrical cables 1906.

A typical protocol for using the AED 1900 is as follows. Initially, the person who has suffered from sudden cardiac arrest is placed on the floor. Clothing is removed to reveal the person's chest 1908. The pads 1904 are applied to appropriate locations on the chest 1908, as illustrated in FIG. 19. The electrical system within the base unit 1902 generates a high voltage between the two pads 1904, which delivers an electrical shock to the person. Ideally, the shock restores a normal cardiac rhythm. In some cases, multiple shocks are required.

Although existing technologies work well, there are continuing efforts to improve the effectiveness, safety and usability of automatic external defibrillators. Accordingly, efforts have been made to improve the availability of automated external defibrillators (AED), so that they are more likely to be in the vicinity of sudden cardiac arrest victims. Advances in medical technology have reduced the cost and size of automated external defibrillators (AED). Some modern AEDs approximate the size of a laptop computer or backpack. Even small devices may typically weigh 4-10 pounds or more. Accordingly, they are increasingly found mounted in public facilities (e.g., airports, schools, gyms, etc.) and, more rarely, residences. Unfortunately, the average success rates for cardiac resuscitation remain abysmally low (less than 1%).

Such solutions, while effective, are still less than ideal for most situations. Assume, for example, that a person suffers from a cardiac arrest in an airport in which multiple AEDs have been distributed. The victim's companion would nevertheless have to locate and run towards the nearest AED, pull the device off the wall, and return to the collapsed victim to render assistance. During that time, precious minutes may have passed. According to some estimates, the chance of surviving a sudden cardiac arrest is 90% if the victim is defibrillated within one minute, but declines by 10% for every minute thereafter. A defibrillator design that reduces the time to defibrillation by even two to three minutes will save more lives.

An additional challenge is that a sudden cardiac arrest may take place anywhere. People often spend time away from public facilities and their homes. For example, a sudden cardiac arrest could strike someone while biking in the hills, skiing on the mountains, strolling along the beach, or jogging on a dirt trail. Ideally, an improved AED design would be compact, light, and resistant to the elements and easily attached or detached from one's body. The typical AED design illustrated in FIG. 19, which includes a sizable console or power unit whose form factor is similar to that of a laptop or backpack, seems less than ideal for the outdoors and other rigorous environments.

New and improved designs are allowing AEDs to become ultra-portable and hence able to be easily carried by an at-risk person as they go about all of their daily activities and thus are able to be close at hand when a sudden cardiac arrest strikes outside of a hospital environment or a high traffic public area with a Public Access Defibrillator.

There are also improvements being made in the area of device usability and ease of operation for untrained bystanders. As noted above, every minute of delay or distraction can substantially decrease the victim's probability of survival. As a result, it is generally beneficial to streamline the operation of the external defibrillator so that a user of the defibrillator, who is presumably under substantial mental duress, can focus his or her attention on a few, key variables.

Another type of defibrillator is the Wearable Cardioverter Defibrillator (WCD). Rather than a device being implanted into a person at-risk from Sudden Cardiac Arrest, or being used by a bystander once a person has already collapsed from experiencing a Sudden Cardiac Arrest, the WCD is an external device worn by an at-risk person which continuously monitors their heart rhythm to identify the occurrence of an arrhythmia, to then correctly identify the type of arrhythmia involved and then to automatically apply the therapeutic action required for the type of arrhythmia identified, whether this be cardioversion or defibrillation. These devices are most frequently used for patients who have been identified as potentially requiring an ICD and to effectively protect them during the two to six month medical evaluation period before a final decision is made and they are officially cleared for, or denied, an ICD.

The current varieties of defibrillators available on the market today, whether Implantable Cardioverter Defibrillators (ICDs) or Automatic External Defibrillators (AEDs) or any other variety such as Wearable Cardioverter Defibrillators (WCDs), predominantly utilize either a Monophasic waveform or Biphasic waveform for the therapeutic defibrillation high-energy pulse or for the lower energy cardioversion pulse. Some clinical research has been done into the benefits of Triphasic waveforms for the therapeutic defibrillation high-energy pulse, but as of yet no device has been brought to market using this type of waveform.

Each manufacturer of defibrillators, for commercial reasons, has their own unique and slightly different take on waveform design for their devices' pulses. Multiple clinical studies over the last couple of decades have indicated that use of a Biphasic waveform has greater therapeutic value to a patient requiring defibrillation therapy, than a Monophasic waveform does, and that Biphasic waveforms are efficacious at lower levels of energy delivery than Monophasic waveforms.

BRIEF DESCRIPTION OF THE DRAWINGS

FIG. 6B illustrates more details of each subsystem of the multiphasic waveform system.

DETAILED DESCRIPTION OF ONE OR MORE EMBODIMENTS

Figure 1:
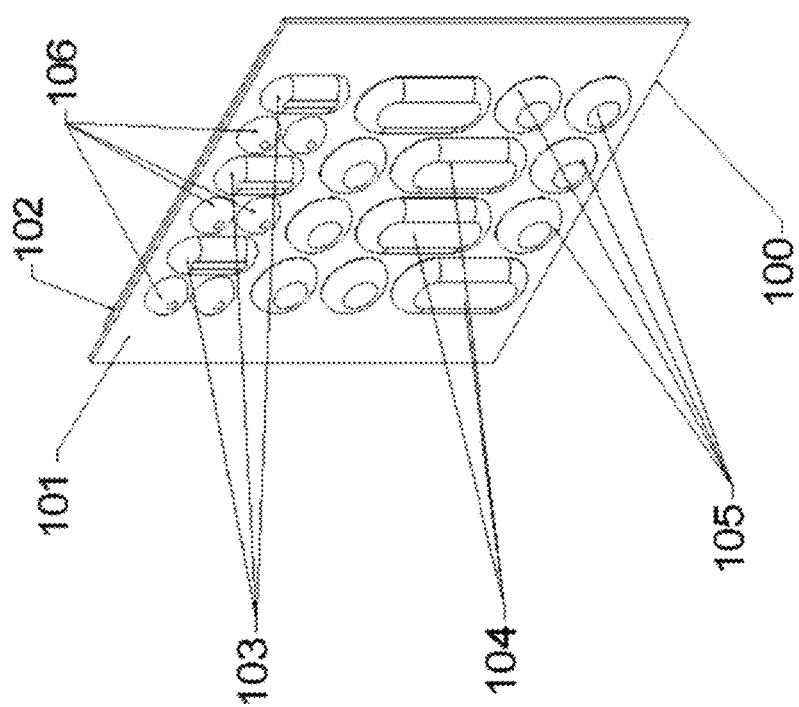
FIG. 1 illustrates an external patient contact assembly exhibiting both sensors and electrodes.

Wearable Cardioverter Defibrillators on the market today are still bulky and uncomfortable for the patients to wear. They utilize a single source of energy in a box that attaches to the wearable garment (containing the sensors and the electrodes) and the energy source box normally rides on the hip. These devices are heavy and uncomfortable to wear and a frequent source of complaints from patients. These existing WCDs also use reservoirs of liquid conductive hydrogel which are deployed onto the patient's skin in contact with the electrodes before a therapeutic shock is delivered in order to reduce the electrode-to-patient impedance. These reservoirs need to be refilled/replaced and the hydrogel needs to be cleaned off the patient on each occasion, both actions of which are an inconvenience or a hassle to the patient and which restrict the ease of using the device in normal daily life. The waveform used in these existing WCDs was originally a monophasic waveform and has now been replaced with a standard biphasic one. This provides a limited range of therapeutic waveforms that can be delivered to a patient.

These existing WCDs also incorporate an override button which a patient can use to prevent unnecessary shocks from being delivered when alerted by an audible alarm that such a shock is about to be delivered. There are medical, practical and commercial needs to make new WCDs smaller and more flexible, more comfortable and more discrete for patients to wear as they go about their daily lives. The most effective way in which to accomplish this, which is disclosed below, has the circuitry and the energy source/reservoir that are re-distributed from one large container/enclosure into several smaller containers each with their own circuitry and energy source/reservoir and which can be mounted in various places on the body of the patient with the sensors and electrodes and hence the system can be made smaller and more flexible, more comfortable and more discrete.

The disclosed system also may use one or more Multi-part Non-uniform Pliable Contact Assemblies that ensures that the optimal electrode contact is maintained with the patient and hence that the electrode-to-patient impedance is minimized without requiring that the patient be dowsed in liquid conductive hydrogel before administering a shock. The system may employ a mix of sensors, such as ECG sensors and LED pulse detectors, rather than the normal use of just ECG sensors, which means that the accuracy of the detection of shockable arrhythmias can be significantly improved and hence the incidence of unnecessary shocks can be significantly reduced and hence the need for a patient to use the override button is reduced.

In one embodiment, the system may use the upper arms of a user as the locations for the circuitry and energy source/reservoir modules which means that the conduction paths for the therapeutic current to reach the heart are of lower impedance than the normal transthoracic conduction pathways. Lowering the patient's impedance means that the device is required to store and deliver less energy and hence the system can be made smaller and more flexible, more comfortable and more discrete.

The system may make use of a plurality of circuitry and energy source/reservoir modules in order to deliver variable amplitude multiphasic waveforms and hence maximize the efficaciousness of the therapeutic shock protocol. In one embodiment, the system may use four modules in order to provide the ability to perform orthogonal shocking such that it maximizes the percentage of cardiac tissue that is depolarized (*Encircling Overlapping Multipulse Shock Waveforms for Transthoracic Defibrillation*; Pagan-Carlo, Allan et al.; December 1998) and hence maximize the efficaciousness of the therapeutic shock protocol. In another embodiment, the system may use six modules in order to provide the ability to deliver overlapping multiphasic waveforms (*Encircling Overlapping Multipulse Shock Waveforms for Transthoracic Defibrillation*; Pagan-Carlo, Allan et al.; December 1998) and hence maximize the efficaciousness of the therapeutic shock protocol.

FIG. 1 illustrates the external patient contact assembly 100 exhibiting both sensors and electrodes wherein the assembly is a multi-part non-uniform pliable contact assembly. The assembly may be made of a pliable substrate 101 with an embedded set of one or more electrode contact elements 104, 105, in various shapes such as bars & buttons, and an embedded set of one or more sensor contact elements 103, 106, in various shapes such as bars & buttons. The various contact elements of the Multi-part Non-uniform Pliable Contact Surface 100 may vary in shape and number to suit the specific need for a given embodiment of the system and its use to provide the best results.

The one or more Electrode Contact Elements (104 and 105) may be a combination of highly conductive Bars (104) and Buttons (105) that provide an interface to the skin of a patient for delivery of the high energy multi-phasic therapeutic shock pulse or lower energy cardioversion pulse. The one or more Sensor Contact Elements (103 and 106) may be a combination of conductive Bars (103) and Buttons (106) that provide an electrical interface to the skin of the patient for the purpose of measuring the weak electrical signals of the heart (ECG), in order to detect abnormal or irregular heart rhythms. Additionally, in one embodiment, some of the Sensor Contact Elements (103 and 106) may be other types of sensors, such as optical sensors utilizing LEDs in order to measure the physical blood flow within the body. By combining the ECG measurements with the physical pulse measurements, the assembly 100 can improve on the speed and accuracy of detection of the abnormal or irregular heart rhythms which are shockable and hence reduce the chance of delivering inappropriate therapeutic shocks to the patient. The one or more electrode contact elements 104, 105 and the one or more sensor contact elements 103, 106 may be arranged in various different configurations on the assembly 100, such as the configuration shown in FIG. 1 in which the sensor contact elements are located across an upper portion of the assembly and the electrode contact elements are located across a lower portion of the assembly.

The materials that the electrode contact elements are made out of are highly conductive and likely to be metallic in nature such as stainless steel, gold, or gold plated copper, silver or another suitable base metal.

The materials that the ECG sensor contact elements are made out of are highly conductive and likely to be metallic in nature such as stainless steel, gold, or gold plated copper, silver or another suitable base metal. Other types of sensors, such as the LED pulse sensors, will be made of different materials. The LED sensors will be made of an optically clear material such as glass, sapphire, plastic or a glass pacified SiGe semiconductor (or other appropriate technology) mounted in such a way as to be in contact with the patient's skin. Other sensor types, such as those for body temperature, skin moisture, acceleration, or other physical properties will be made of the materials relevant to the specific need involved and these are likely to be well known in the art for each.

Figure 2:
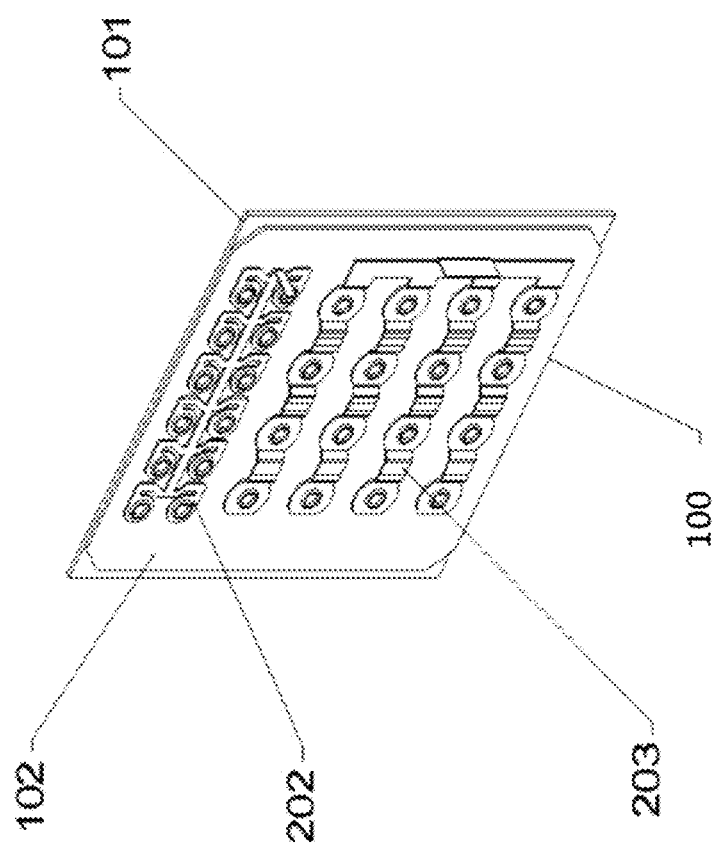
FIG. 2 illustrates the reverse side of the assembly in FIG. 1 exhibiting the internal electrical contacts and anchor locations.

FIG. 2 shows the back side for the Multi-part Non-uniform Pliable Contact Assembly (100). On the back side, the conductive Electrode and Sensor Contact Elements (104 and 105, 103 and 106) are attached to one or more Pliable Substrates (101 and 102) that allow the assembly 100 with the contact elements to bend and flex. The backside of the assembly 100 may also have one or more circuit assemblies 202, 203 that interconnect the conductive Electrode and Sensor Contact Elements (104 and 105, 103 and 106.) The Electrode and Sensor Contact Elements (104 and 105, 103 and 106) are installed and through a swage process, the ends of the contact elements are rolled over forming a solid physical and electrical contact to the Interconnecting Circuit Assemblies (202 and 203). In the embodiments where they are used, the alternative (optical and non-metallic) Sensor Contact elements are attached as appropriate to their specific purposes.

Figure 3:
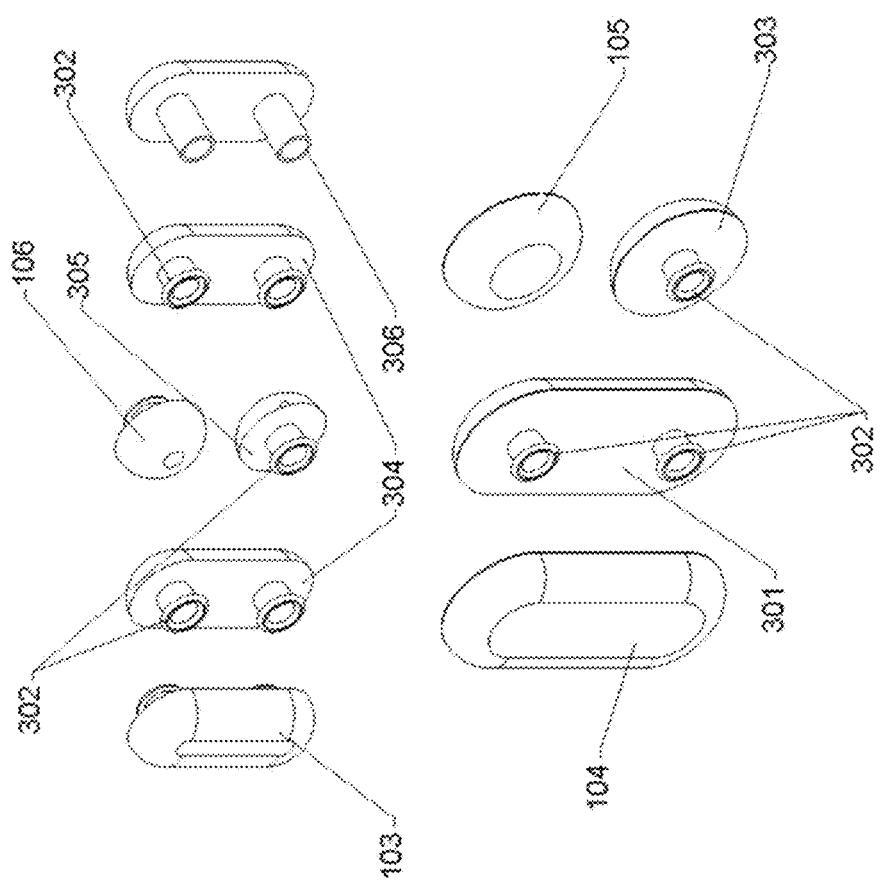
FIG. 3 illustrates various shaped sensor and electrode components of the assembly in FIG. 1 before and after being swaged.

FIG. 3 shows the details of the conductive Electrode and Sensor Contact Elements (104 and 105, 103 and 106). A back side of the Electrode and Sensor Contact Elements (301 and 303, 304 and 305) are shown and the result of the swage process is illustrated. An end of the contact (306) is shaped as a hollow tube, that is rolled over through the use of a die and forms the end into an expanded disk (302) for each of the contact elements. The expanded disks 302 of each contact element may then be sandwiched between the Pliable Substrates (101 and 102) and the Interconnecting Circuit Assemblies (202 and 203), forming the physical and electrical connections.

Figure 4:
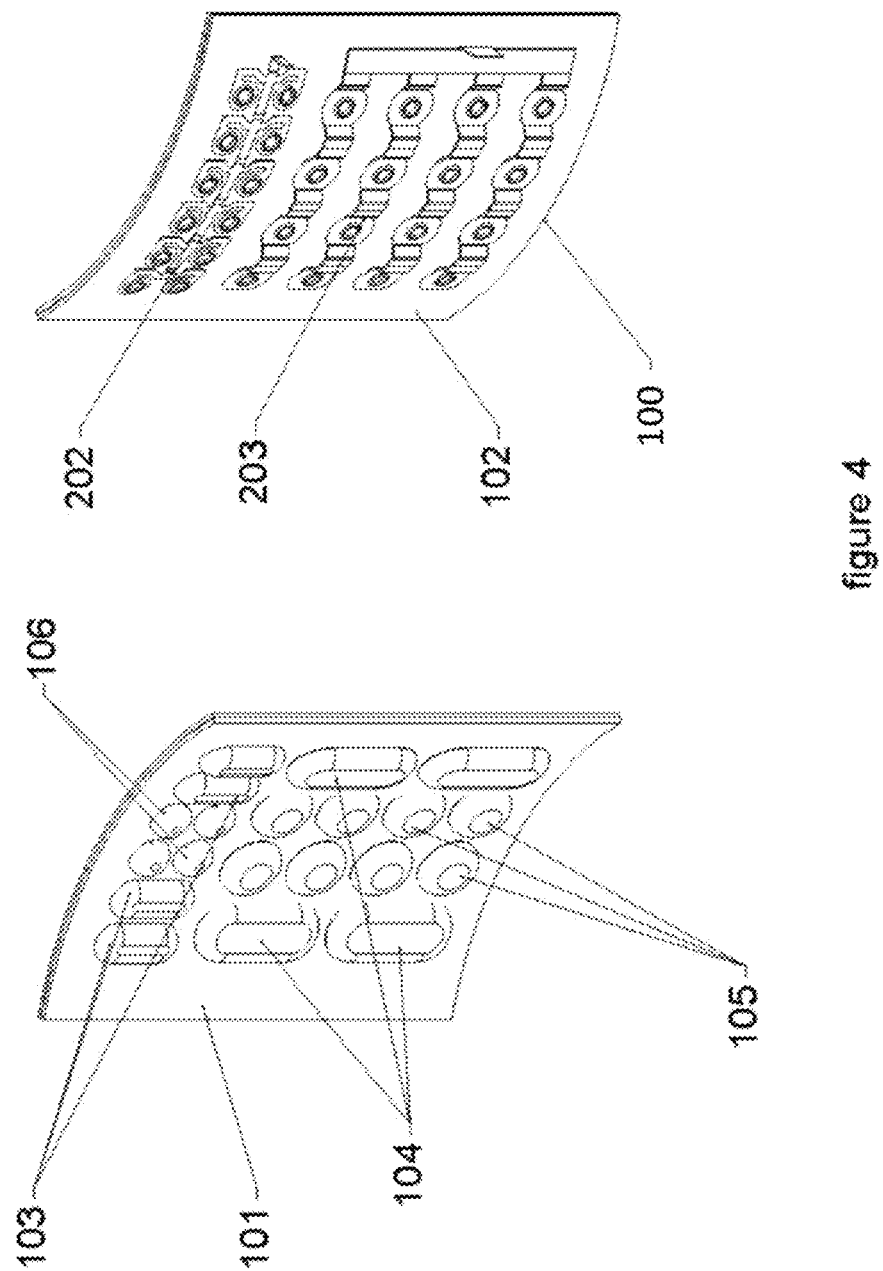
FIG. 4 illustrates both sides of an external patient contact assembly while in a flexed position.
Figure 8:
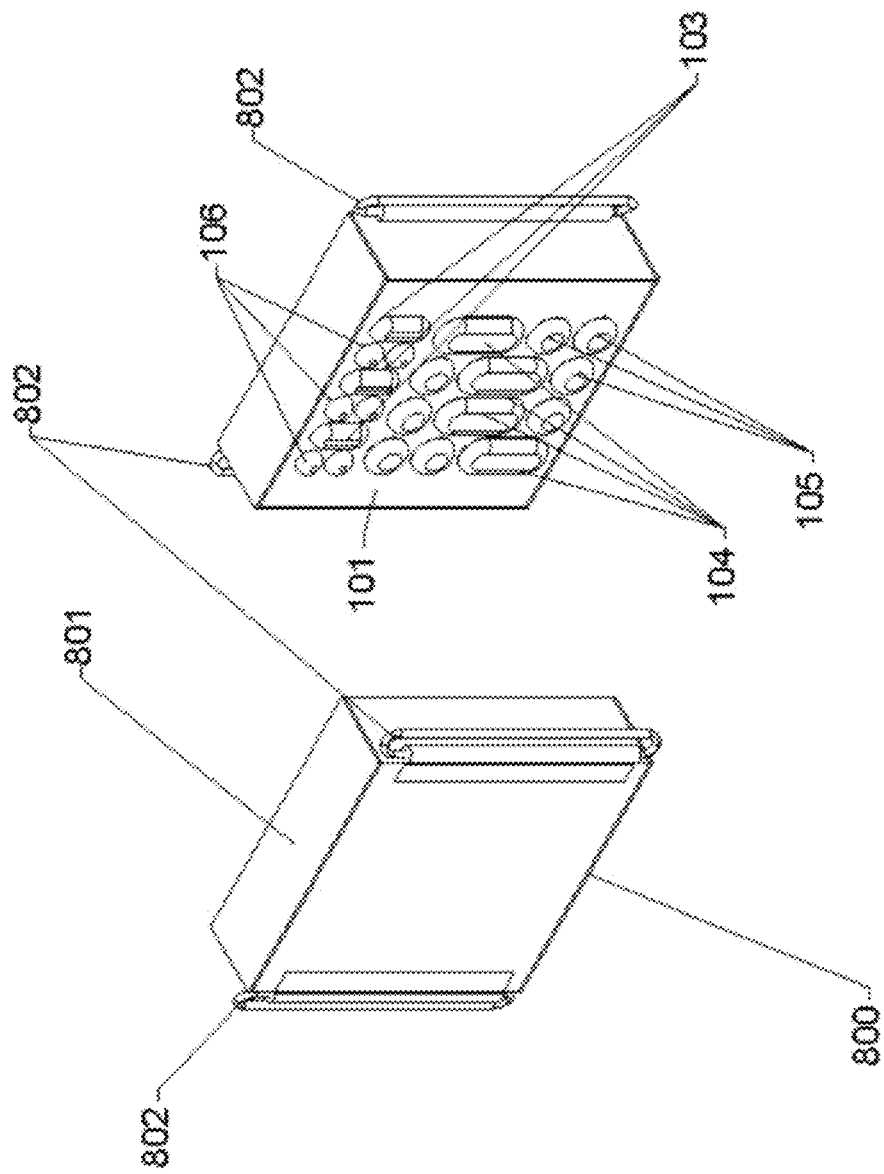
FIG. 8 illustrates circuitry and energy source/reservoir module with strap attachment fixtures.
Figure 9:
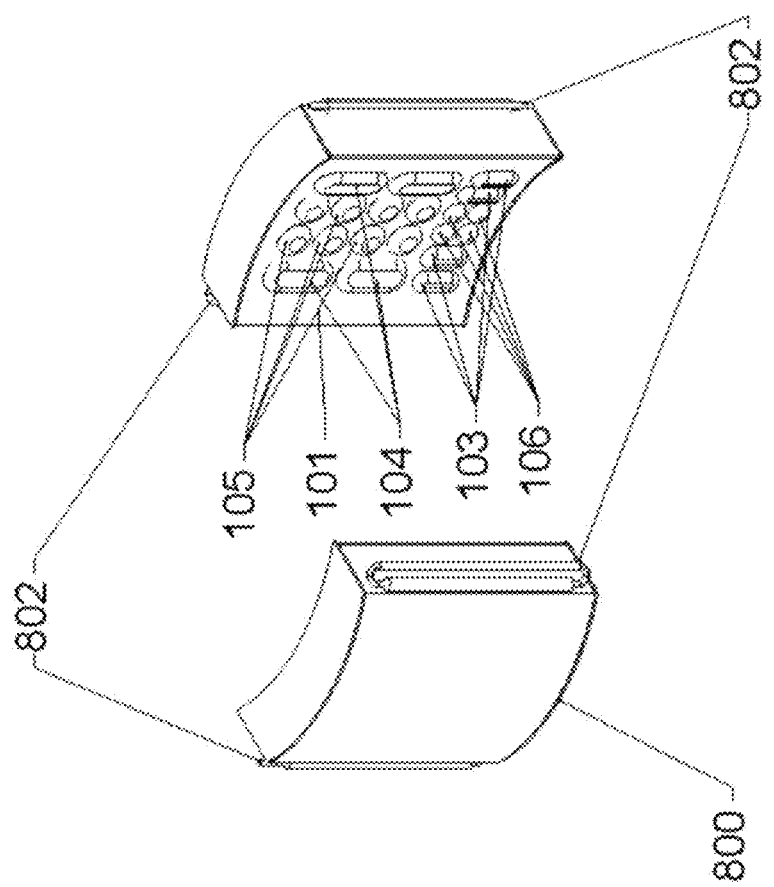
FIG. 9 illustrates a flexed circuitry and energy source/reservoir module with strap attachment fixtures of FIG. 8.

FIG. 4 illustrates both sides of the external patient contact assembly 100 while in a flexed position. The assembly 100 may be fabricated on the set of Pliable Substrates (101 and 102). The outer Pliable Substrate (101) is made of a tightly woven material that is hypo-allergenic and gentle and yet also very strong. An example of this is a silicon, nylon reinforced material, although suitable new materials are being created all of the time. This material will constitute the outer surface of the AED High Energy Source/Reservoir circuitry as shown in FIGS. 8 and 9. The inner Pliable Substrate (102) may be made of a sheet of flexible material, such as reinforced flexible nylon. The inner Pliable Substrate (102) provides stabilization and precise locations for the Electrode and Sensor Contact Elements (104 and 105, 103 and 106) and a stable backing structure for the Interconnecting Circuit Assemblies (202 and 203). The Multi-part Non-uniform Pliable Contact Assembly (100) is shown in FIG. 4 in a curved state. The assembly 100 may be flexed in all axes. The assembly 100 supports the ability of the contact assembly 100 to maximize contact with the patient when being used to deliver a shock to the patient, such as by a wearable AED.

Figure 5:
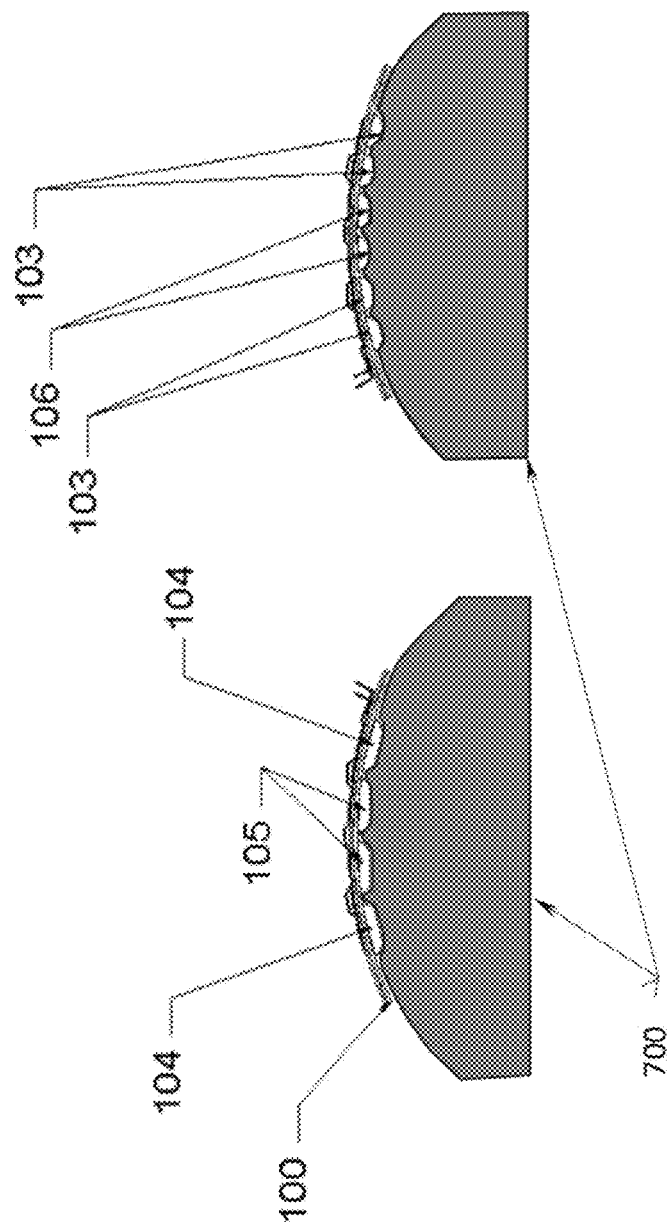
FIG. 5 illustrates the contact between a patient's skin and the patient contact assembly of FIG. 4.

FIG. 5 illustrates the contact between a patient's skin and the patient contact assembly (patient interface). As shown in FIG. 5, the front (contact with Patient) surfaces of the Electrode and Sensor Contact Elements (104 and 105, 103 and 106) have gentle curved smooth surfaces, providing comfort to the Patient skin, while allowing the pliable dermis/epidermis layers to deform, wraparound and conform to the embedded shapes of the Bar and Button contacts, as shown in FIG. 5. The Electrode and Sensor Contact Elements (104 and 105, 103 and 106) are shown in contact with the Patient's skin, 700. The pliable nature of the Patient's dermis/epidermis layers effectively fills in the gaps between the Bar and Button Contact Elements, in addition the flexible nature of the Pliable Contact Assembly (100) increases and maximizes the contact areas with the Patient by conforming to the specific curvatures of the body.

Figure 6A:
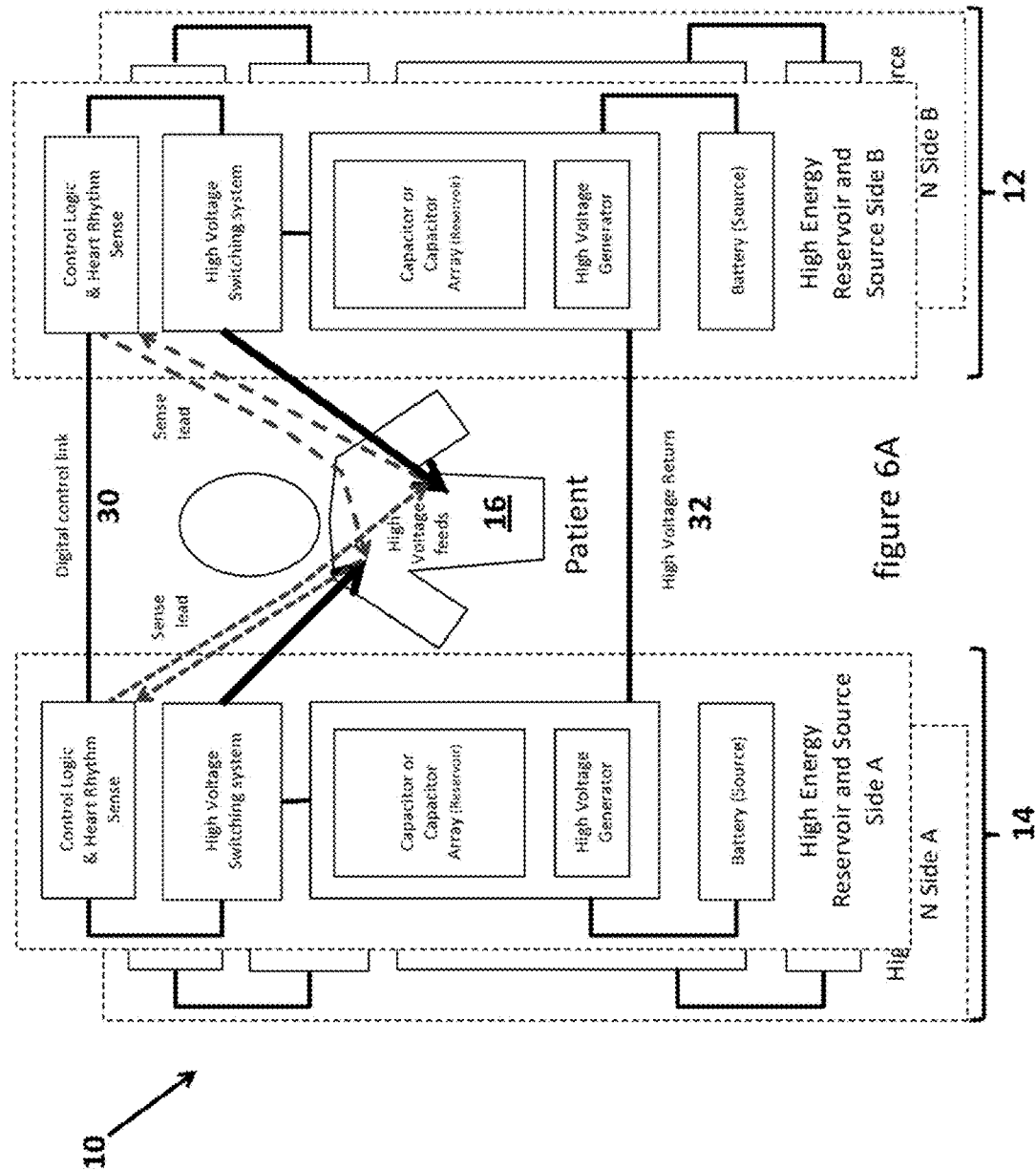
FIG. 6A illustrates a multiphasic waveform system with a plurality of independent subsystems each with its own energy reservoir and energy source.
Figure 7:
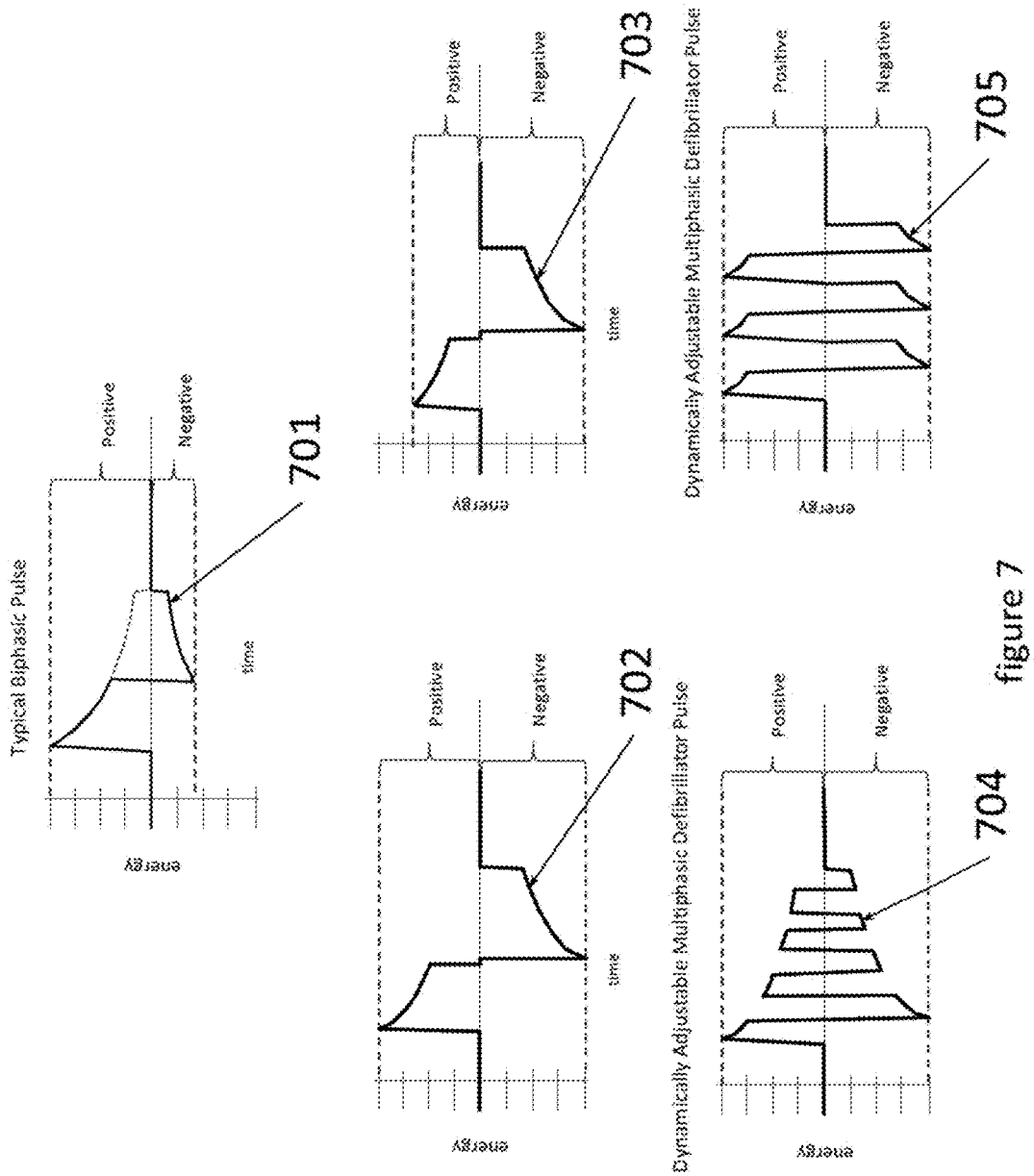
FIG. 7 illustrates defibrillator pulse waveforms including a typical biphasic pulse waveform and four novel biphasic pulse and multiphasic pulse waveforms.

FIG. 6A is a block diagram of a multiphasic waveform system with a plurality of independent subsystems each with its own energy reservoir and energy source that may be used as part of the wearable AED. The pulse system 10 is not limited to any particular number of energy reservoirs (such as capacitors) or energy sources (such as batteries). The pulse system 10 may have a plurality or "n" number (as many as wanted) subsystems 12, 14 that together can be utilized to provide the various multiphasic waveforms, examples of which are shown in FIG. 7 and described below. In the example implementation shown in FIG. 6A, there may be two sides, such as side A and side B as shown, and each side may have one or more of the subsystems 12, 14 and each subsystem may generate a pulse (that may be a positive pulse or a negative pulse.) The two or more subsystems 12, 14 permit the system to shape the various characteristics of a positive phase of the waveform separately from the shaping of the characteristics of the negative phase of the waveform and vice versa. The above described functions may be accomplished through the use of a fast switching high-energy/voltage switch system as described below.

Each subsystem 12, 14 of each side, as shown in FIG. 6B, may have a control logic and heart rhythm sense component 20 (that is connected to a similar component on the other side by a digital control link 30 as shown in FIG. 6A) that may be also coupled to a high voltage switching system component 22. The high voltage switching system component 22 may be implemented using either analog circuits or digital circuits or even some hybrid of the two approaches. Furthermore, the high voltage switching system component 22 may be implemented through the use of mechanical or solid-state switches or a combination of the two. As shown in FIG. 6D, the high voltage switching system component 22 may be implemented using one or more semiconductor circuits, such as the insulated gate bipolar transistors. The high voltage switching system component 22 may be coupled to an energy reservoir 24 and the energy reservoir 24 may be coupled to a power source 26, such as a battery. The energy reservoir 24 may further comprise a reservoir 24A, such as for example one or more capacitors or a capacitor array, and a high voltage generator 24B. The energy reservoir 24 may also be coupled, by a high voltage return line 32 to the other side of the system as shown in FIG. 6A. The high voltage return 32 electrically completes the circuit and is present in existing defibrillators, but in a slightly different form since in the existing style of devices it is split into two parts: in the form of the two leads which go from the main defibrillator device to the internal or external surface of the patient.

The control logic and heart rhythm sense component 20 is well known in the art and the component analyzes the ECG signals from the patient for treatable arrhythmias and then chooses to shock the patient when a treatable arrhythmia is detected, along with guiding the operator through both visual and audible means through this process when the device is of the external automated variety. The control logic and heart rhythm sense component 20 also may control and shape the therapeutic pulse as it is delivered from the energy reservoir and ensures that it is as optimal as possible for the individual patient. In the implementations shown in FIG. 6A, the control logic and heart rhythm sense component 20 may generate the therapeutic pulse using the one or more groups of subsystems since each subsystem may have its own control logic 20 (so that each of them can control just the portion/phase of the pulse/waveform that they deliver. This provides a much higher level of control over what range of waveform shapes can be used/delivered, including many that are not possible with the existing devices. This also provides better weight and size distribution, as well as size and weight reductions, and the ability to have the devices look radically different and be handled in very different ways—ones that are much more operator intuitive. The disclosed system also provides a much higher level of redundancy and fault mitigation for the device embodiments that use it.

In one implementation, each control logic in each subsystem may have a circuit that can be used to adjust the shape of each portion of the therapeutic pulse. The circuit, may be for example, an array of resistors of various strengths and switches so that one or more of the resistor may be selected (as an array of selectable resistors) that can optimize and alter an RC constant of a subsystem's pulse phase generating circuitry in order to dynamically shape one or more pulse phases.

In some embodiments of the system, the system may provide for the recharging of individual energy reservoirs by the energy sources during times (including inter-pulse times) that an individual energy reservoir is not selected for discharge as shown in FIG. 6A. This provides the opportunity to interlace equivalent amplitude initial multiphasic pulses utilizing several different high energy reservoirs as shown in FIG. 7. Alternatively, each module may have one of a rechargeable or replaceable energy sources or a combination of the two. In some implementations, the each module may contain sufficient energy for only a limited number of life saving shocks.

In one implementation, the system 10 has side A that may deliver one or more of a Positive phase waveform of the Multiphasic therapeutic pulse and Side B may deliver one or more of a Negative phase waveform of the Multiphasic therapeutic pulse. As shown in FIG. 6A, the subsystems may be coupled to the patient 16 by one or more high voltage leads and one or more sense leads wherein the high voltage leads deliver the therapeutic pulse and the sense leads are used to detect the heartbeat by the control unit.

The system 10 may either be pre-programmed to use a specific single multiphasic pulse shape, according to which one is shown to be most efficacious in clinical lab testing/trials, or else it may select the best one for a given purpose from a lookup table where they are listed according to their suitability for optimally resolving different types of arrhythmia that are being screened for and identified or for the different treatments as described above. Regardless, the system and method allows the use and application of a much wider range of pulse shapes than has been previously possible and this will allow the devices which use this invention to keep up with clinical developments as waveforms continue to be improved.

Figure 6C:
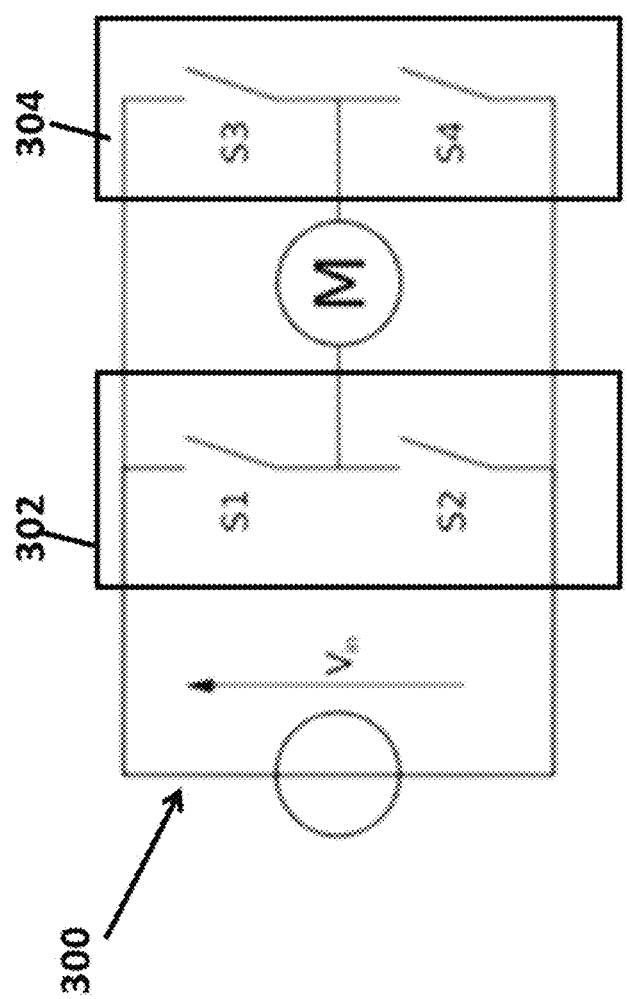
FIG. 6C illustrates a typical H-bridge circuit.
Figure 6D:
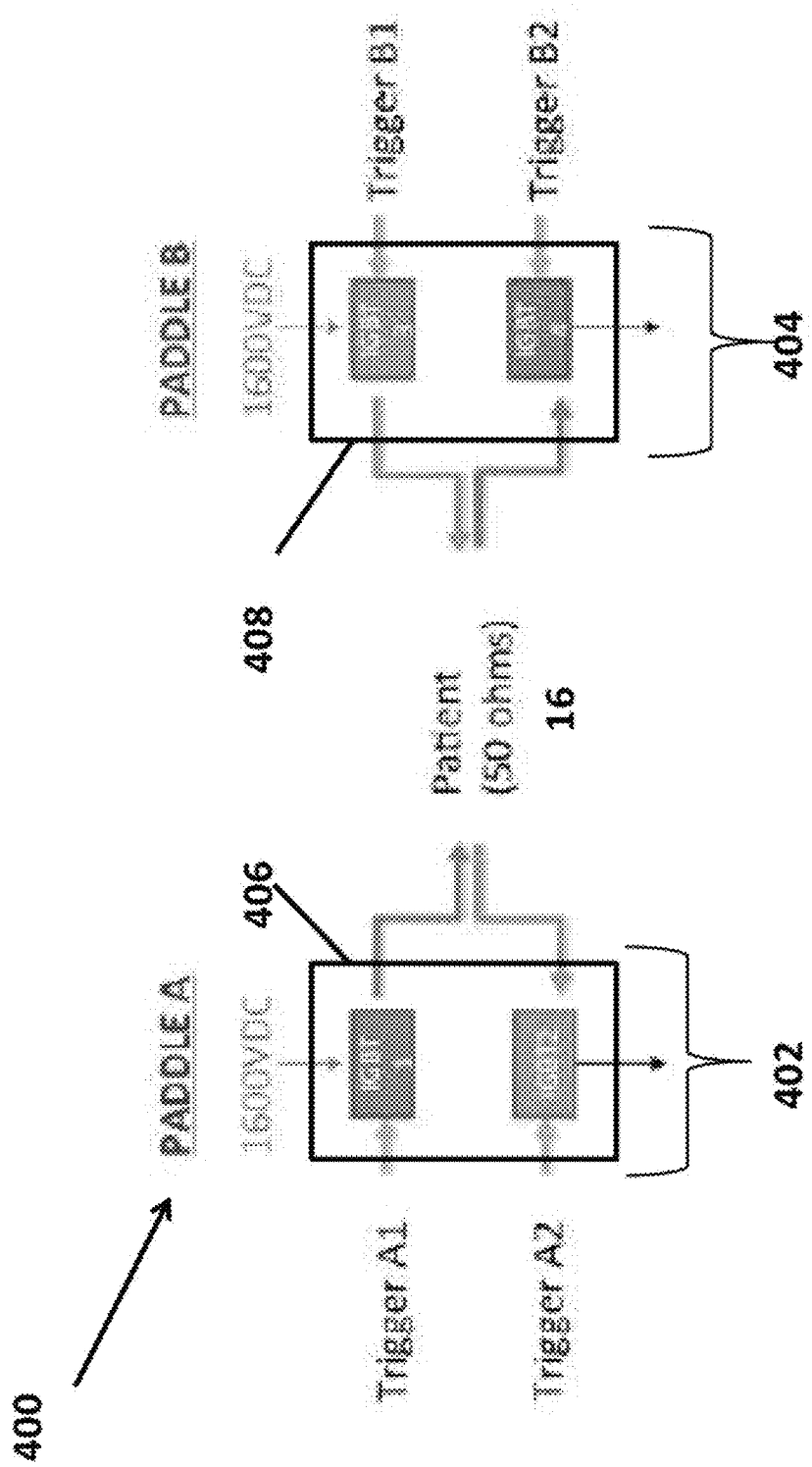
FIG. 6D illustrate an H-bridge circuit integrated into the multiphasic waveform system

FIG. 6C illustrates a typical H-bridge circuit 300 and FIG. 6D illustrates an H-bridge circuit concept used in the multiphasic waveform system. As shown in FIG. 6C, an H-bridge circuit is a known electronic circuit that enables a voltage, such as Vin, to be applied across a load, M, in either direction using one or more switches (S1-S4) (see http://cp.literature.agilent.com/litweb/pdf/5989-6288EN.pdf that is incorporated by reference herein for additional details about the H-bridge circuit.) As shown in FIG. 6C, the H-bridge circuit may have a first portion 302 and a second portion 304 that form the complete H-bridge circuit.

As shown in FIG. 6D, the H-bridge circuit may be part of the control circuits or switching systems shown in FIGS. 6A and 6B. The load of the H-bridge circuit in the multiphasic system is the patient 16 (shown here as having the industry simulation standard resistance of 50 ohms, but which can vary between 20 and 200 ohms with real patients) to which the therapeutic pulse is going to be applied to provide treatment to the patient. The treatment to the patient, depending on the power and/or energy level of the therapeutic pulse may be for cardiac pacing, cardioversion, defibrillation, neurological therapy, nerve therapy or musculoskeletal therapy. Each side of the multiphasic system may generate its energy as described above and an H-bridge circuit 400 may be used to apply two (or more) unique energy sources to the single load. In the example shown in FIG. 4, each side of the system (such as side A and side B shown in FIGS. 6A and 6B) may have a portion 402, 404 of the H-bridge so that the multiphasic system has a complete H-bridge circuit that is combination of portions 402, 404. The multiphasic system may then be used to deliver the therapeutic pulse through defibrillation paddles, such as Paddle A and Paddle B as shown in FIG. 4) to the patient.

Each portion 402, 404 of the H-bridge has its own energy source, 1600 VDC in the example in FIG. 6D. In each portion of the H-bridge, the energy source may be switched using switches 406, 408 to make contact with the patient at a separate but specific time. The switches for each portion may be part of the switching system shown in FIGS. 6A and 6B. In the example in FIG. 6D, each portion may have two switches and each switch may be a commercially available insulated-gate bipolar transistor (IGBT.) Each switch may be controlled by a separate trigger signal as shown to discharge the energy to the patient. This provides for the two or more energy sources to discharge their energy to the load (patient) at a precise time, generating a resulting Biphasic discharge pulse or other therapeutic pulse shapes (examples of which are shown in FIG. 7) as defined for an application, or therapeutic condition.

FIG. 7 illustrates the pulse waveform capabilities of the dynamically adjustable multiphasic defibrillator pulse system. Pulse 701 shows a typical Biphasic Defibrillator Pulse with an exponentially declining amplitude, and 702; 703; and 704 show the capability of the dynamically adjustable multiphasic defibrillator pulse system to produce Biphasic and Multiphasic waveforms that have the following characteristics: equal amplitude in the initial positive and negative phases of the pulse (702), to produce a waveform with an initial lower amplitude positive phase and an initial higher amplitude negative phase pulse (703) and also to produce a waveform with equal amplitude in the initial positive and negative phases of the pulse and multiple positive phase to negative phase pulse transitions (704). 705 shows the ability for the pulse system to provide a waveform with equal amplitude in all of the positive and negative phases of the pulse and with multiple positive phase to negative phase transitions throughout the entire therapeutic pulse event.

These waveforms can start with either a positive or a negative polarity phase. Phases subsequent to the first phase can also be of a lower leading edge amplitude than would be expected from the trailing edge of the prior phase. The tilt (or rate of the phase's signal decay) can also vary from phase to phase through the use of varying capacitor ratings within the capacitors constituting each energy reservoir or else through the use of suitable resistors.

Figure 10:
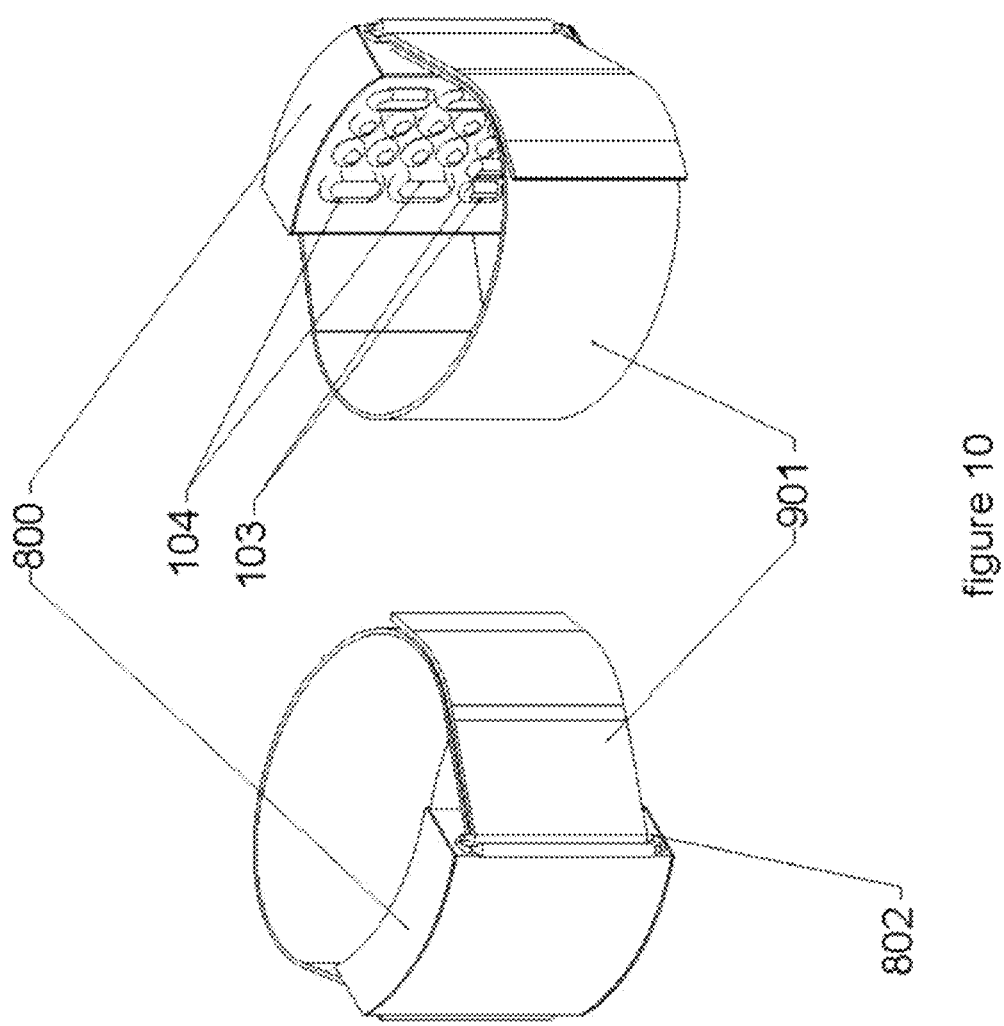
FIG. 10 illustrates a couple of flexed circuitry and energy source/reservoir modules with straps for attachment to a patient's torso and/or limbs.

FIG. 8 illustrates a circuitry and energy source/reservoir module 800 with strap attachment fixtures. The wearable multiphasic system may have one or more of the circuitry and energy source/reservoir module 800 attached to the body of the patient. Each of the one or more circuitry and energy source/reservoir modules (800), is housed in a pliable and flexible outer shell (801), shown in two different embodiments in FIGS. 8 and 9. The outer shell (801) may be made of a material that is highly durable and flexible, similar to the woven nylon found in aviator/space suits. The mounting bands (901) shown in FIG. 10 are attached to rings (802) that are connected to the housing of the outer shell (801). The Multi-part Non-uniform Pliable Contact Assembly (100) and the Electrode and Sensor Contact Elements (104 and 105, 103 and 106) are, in one embodiment, incorporated within the flexible outer shell (801). In some implementations, each module 800 may have an adhesive on or around the patient interface assembly (including the multi-part non-uniform pliable contact assembly (100) and the electrode and sensor contact elements (104 and 105, 103 and 106)) to help the patient interface assembly remain in place on the patient while being worn by the patient as shown in FIGS. 14-18.

FIG. 9 shows an embodiment with the ability for each of the circuitry and energy source/reservoir modules (800) to conform to the patients' body curves. FIG. 10 illustrates a couple of flexed circuitry and energy source/reservoir modules with straps for attachment to a patient's torso and/or limbs. In one or more of the embodiments of the system, the housing/shell 800,801 (see FIGS. 8-10 and 12A and 12B for different examples) may be waterproof so that the circuitry and elements in the housing/shell are protected from water damage.

FIG. 10 shows one of the plurality of circuitry and energy source/reservoir modules (800) with a mounting band (901) attached wherein the mounting band may have different sizes. The bands of differing sizes allow for mounting each of the plurality of circuitry and energy source/reservoir modules (800) to various locations on the patient. In one embodiment, the wearable multiphasic AED system may have at least two such modules (800), as shown in FIG. 10, to constitute a functional Wearable Cardioverter Defibrillator. However, the embodiments of the system are not limited to the use of just two modules 800, as there can be 1 to N number of modules in various embodiments of the system wherein N may be between 1 and 100.

Figure 11:
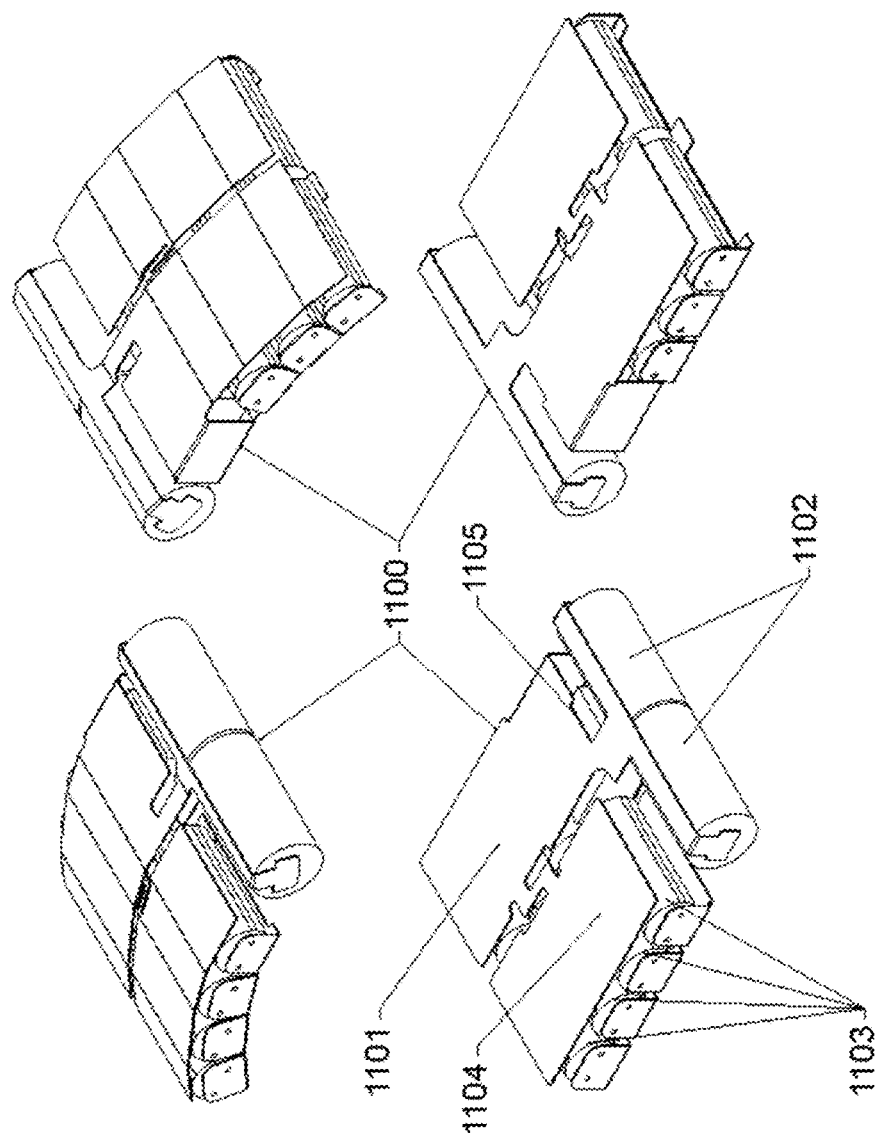
FIG. 11 illustrates the components and flexible circuitry within a circuitry and energy source/reservoir module in both flexed and non-flexed states.
Figure 12:
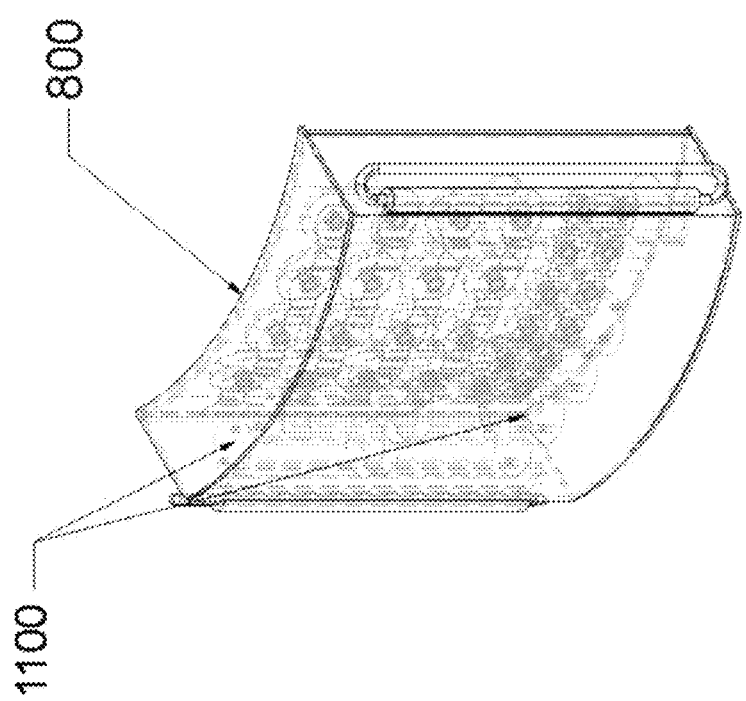
FIGS. 12A and 12B illustrate a space within a circuitry and energy source/reservoir module for the components and flexible circuitry that is used in the module.
Figure 12B:
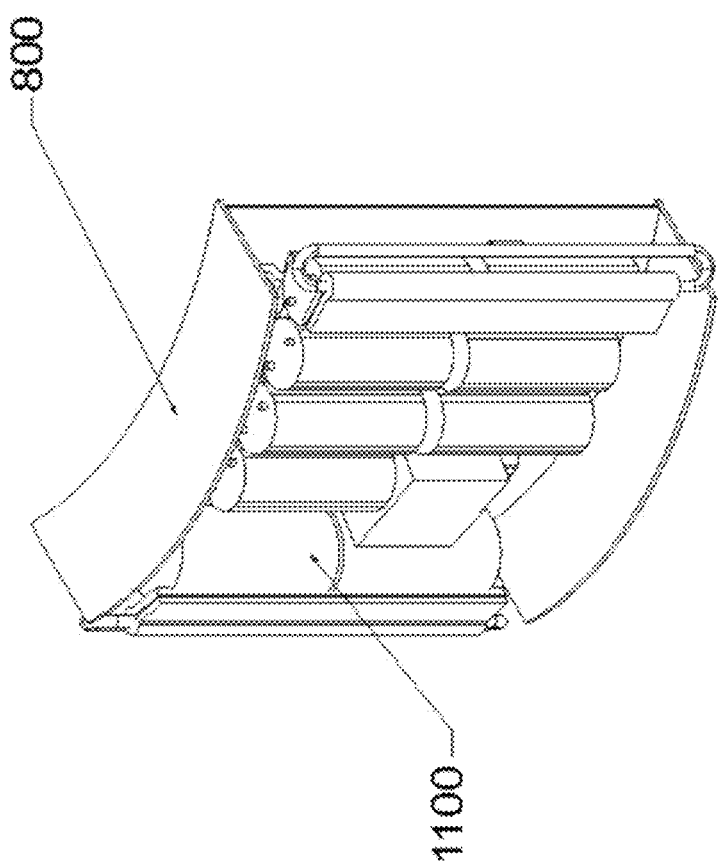

A reference high voltage return lead and a digital control link (1405) shown in FIGS. 6 and 14-18, connects the plurality of circuitry and energy source/reservoir modules (800) together in whatever connection combinations are therapeutically desirable. The Digital Control link 1405 connects the Control Logic & Heart Rhythm management systems of the modules (800) together and coordinates the sensing and therapeutic action decisions and various other Automated External Defibrillator or Wearable Cardioverter Defibrillator functions. The High Voltage return lead(s) provide the reference and return electrical path for the Therapeutic shock pulse. FIG. 11 illustrates the components and flexible circuitry within a circuitry and energy source/reservoir module 1100 in both a flexed state and a non-flexed state. The high energy source/reservoir (1100) is made up of one or more energy reservoirs 1103, such as one or more capacitors, a high voltage generator (1105), a high voltage switching system (1101), one or more energy sources 1102, such as one or more batteries and a control logic & heart rhythm sense/management control system (1104). All of these components or subsystems are well known in the art. The High Energy Source/Reservoir may be constructed of discreet components attached and interconnected through a Flex circuit board that allows the High Energy Source/Reservoir to conform with the Multi-part Non-uniform Pliable Contact Assembly (100) and with the module (800) to the patient's body. FIGS. 12A and 12B show the High Energy Source/Reservoir (1100), within the module (800) in which the other side of the module 800 has the assembly 100.

Figure 13:
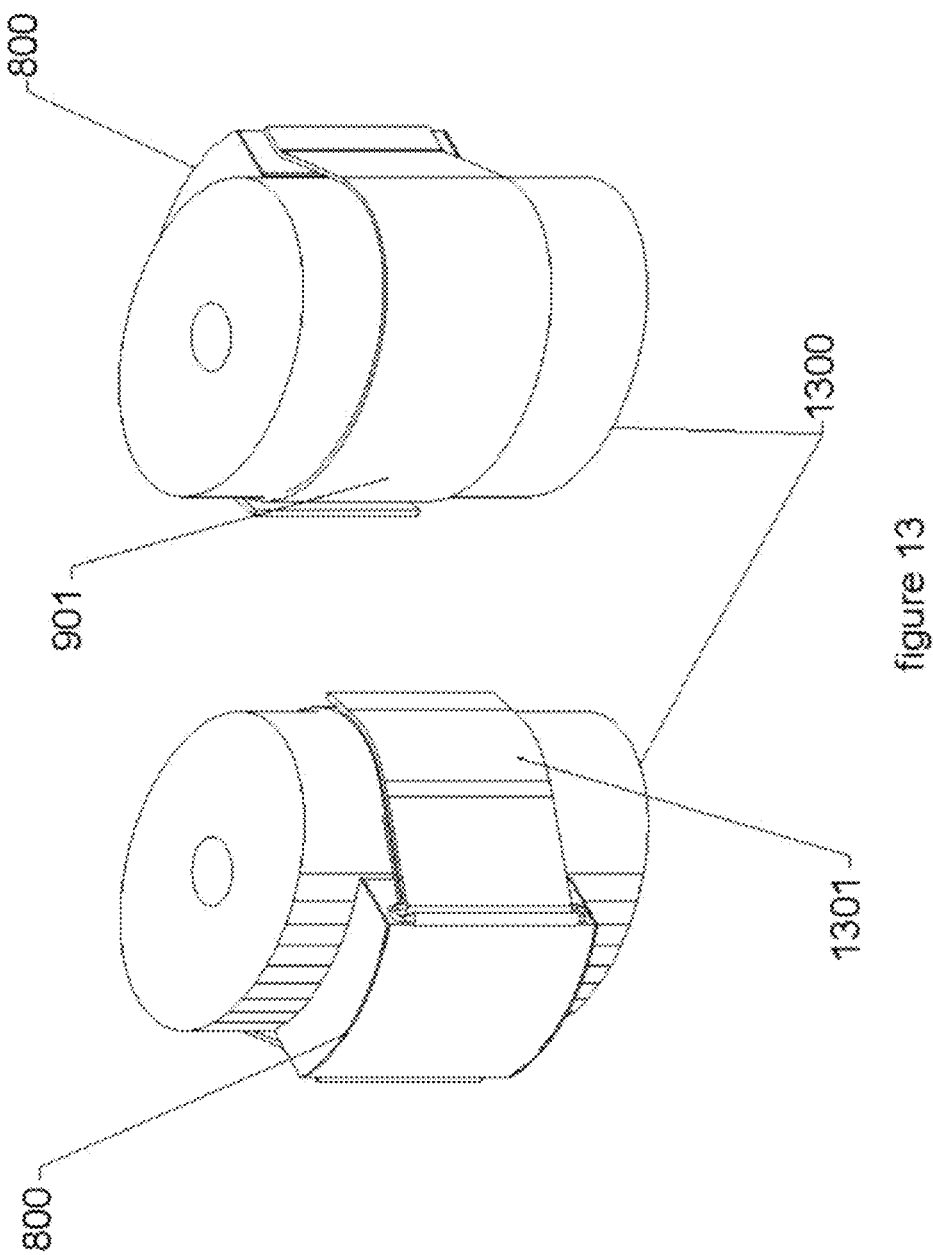
FIG. 13 illustrates how a circuitry and energy source/reservoir module with strap attaches to a patient's torso and/or limb.

FIG. 13 illustrates how a circuitry and energy source/reservoir module 800 with strap 901 attaches to a patient's torso and/or limb 1300. In this embodiment the patient would attach the module (800) to their arm(s) (1300) and pull the mounting band (901) and then press the loose end (1301) to an anchor (made of a material such as Velcro) on the mounting band (901). This allows the patient to adjust the tension to be comfortable whilst still ensuring that an optimal contact is maintained across the Multi-part Non-uniform Pliable Contact Assembly (100).

In addition to the circuitry and elements of the modules described above, the system may also have additional sensors, location sensing circuitry (such as GPS or other current or future equivalent standards); communications circuitry (such as cellular, satellite, Wi-Fi, Bluetooth or other current or future equivalent standards); additional energy sources, data storage or external data storage for the detected signals of the patient's heart, or external/remote processing capabilities. Some of the these additional elements may be, for example, implemented in circuits within the modules or within the housing of the modules or in any known manners. The system may then interact with these additional elements.

Figure 14:
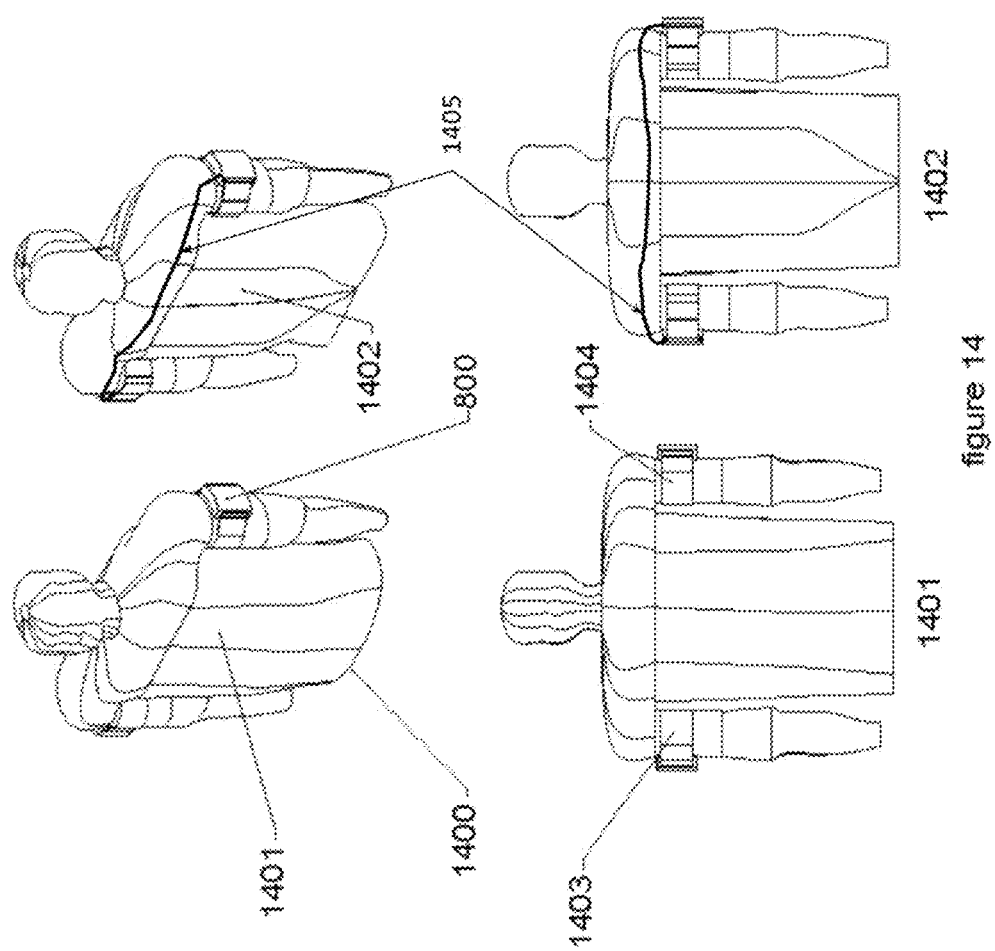
FIG. 14 illustrates an embodiment with two modules, both mounted on the exterior of the upper limbs and electrically connected.

The flexibility of the usable configurations of the invention when using two or three modules is shown in FIGS. 14, 15, 16, 17 and 18, but it is not limited to the embodiments shown in these examples. The system modules (800) can be mounted "outbound" on the externally facing surface of each upper arm (1403 and 1404) as shown in FIG. 14 in the front view (1401) and back view (1402). The location utilizes the vascular system of the patient's arms to conduct the therapeutic shock directly to the heart.

Figure 15:
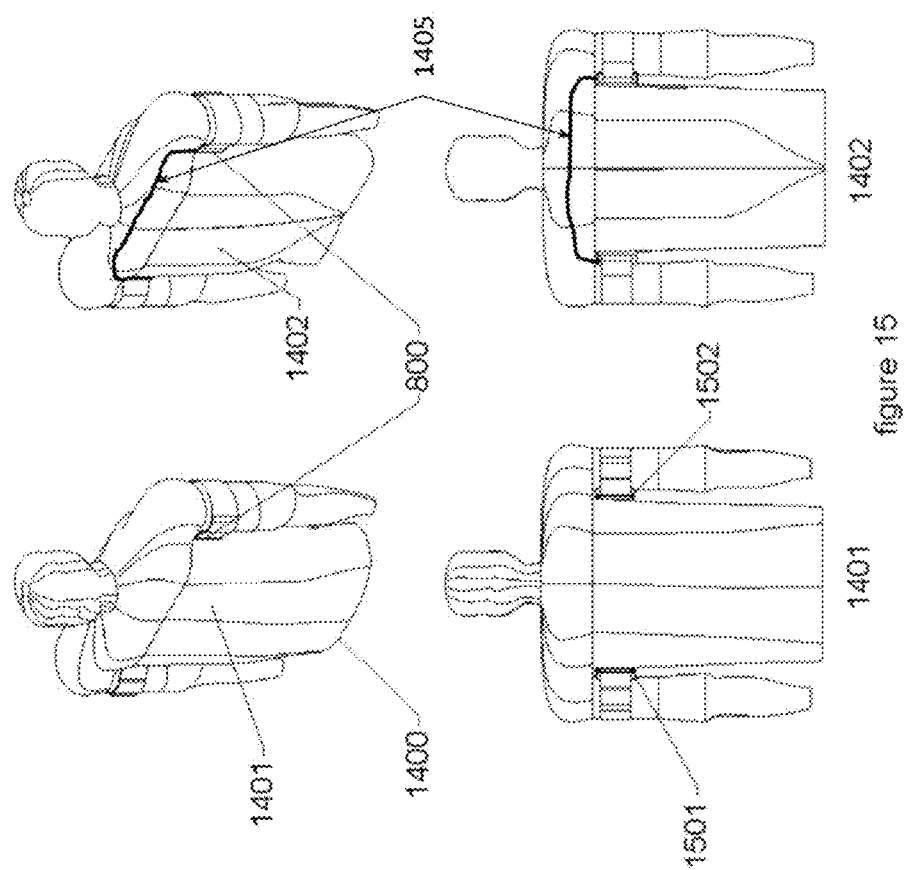
FIG. 15 illustrates an embodiment with two modules, both mounted on the interior of the upper limbs and electrically connected.
Figure 16:
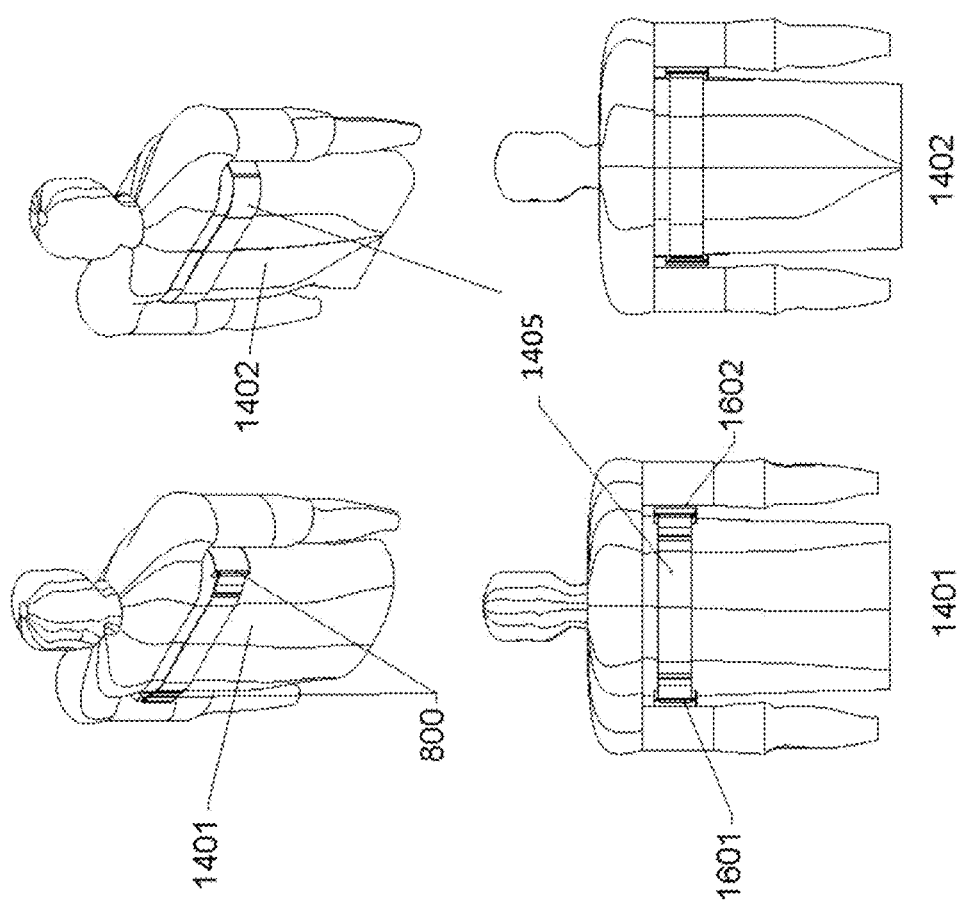
FIG. 16 illustrates an embodiment with two modules, both mounted on the torso under the upper limbs and electrically connected via the mounting strap(s).

FIG. 15, shows that the modules (800) can also be mounted "inbound" on the internally facing surface of each upper arm (1501 and 1502) as shown in the front view (1401) and back view (1402). The location utilizes the vascular system of the patient's arms to conduct the therapeutic shock directly to the heart. FIG. 16, shows the modules (800) can be mounted under the arms on the upper chest (1601 and 1602) as shown in the front view (1401) and back view (1402). An alternate band(s) containing the reference high voltage return lead and digital control link (1405) is utilized to mount and interconnect the modules (800) for this embodiment. The location utilizes the thoracic cavity conductive pathways of the patient to conduct the therapeutic shock to the heart.

Figure 17:
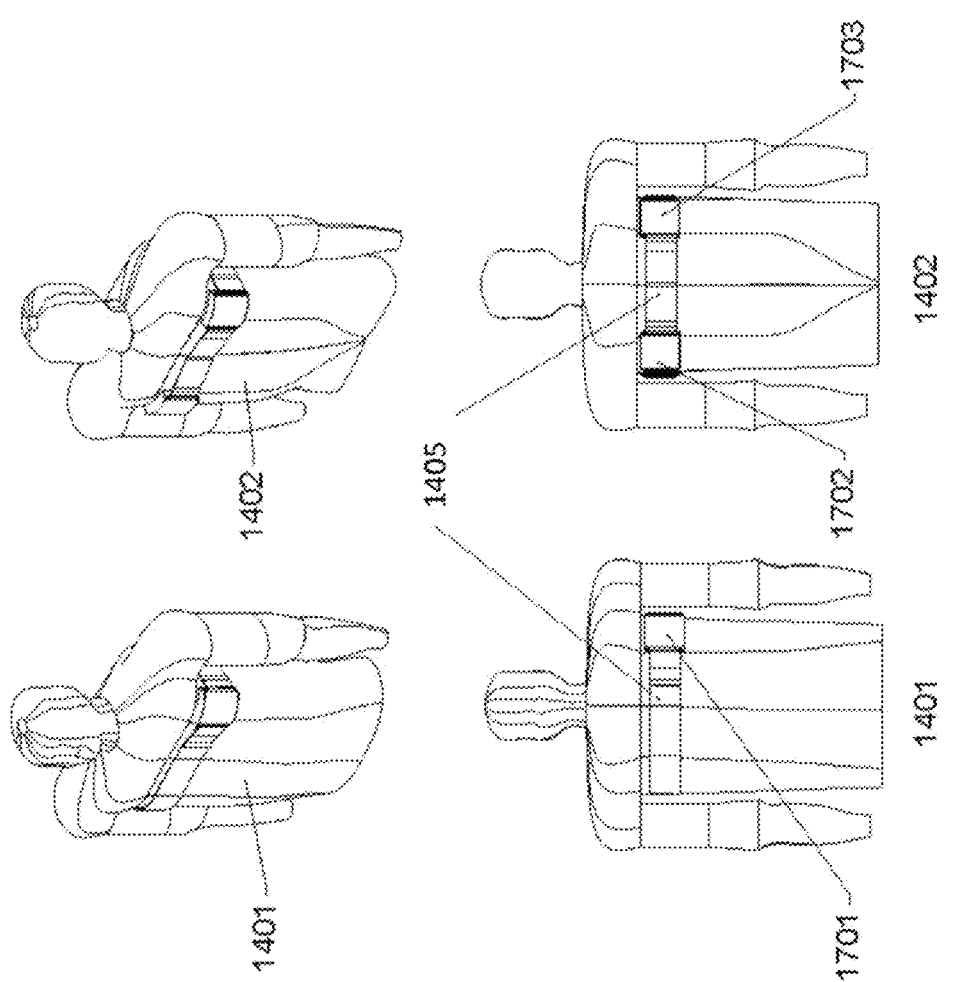
FIG. 17 illustrates an embodiment with three modules, all mounted on the torso of the patient and electrically connected via the mounting strap(s).

FIG. 17, shows an embodiment where three (3) modules (800) are mounted on the upper chest (1701, 1702 and 1703) as shown in the front view (1401) and back view (1402). An alternate band(s) containing the reference high voltage return lead and digital control link (1405) is utilized to mount and interconnect the modules (800) for this embodiment. The location utilizes the thoracic pathways of the patient to conduct the therapeutic shock to the heart. The third module provides an additional energy source/reservoir, hence expanding the capability of the invention by providing additional/alternate thoracic conduction routes for delivering the therapeutic pulse as well as an additional energy source/reservoir for shaping the nature of the pulse.

Figure 18:
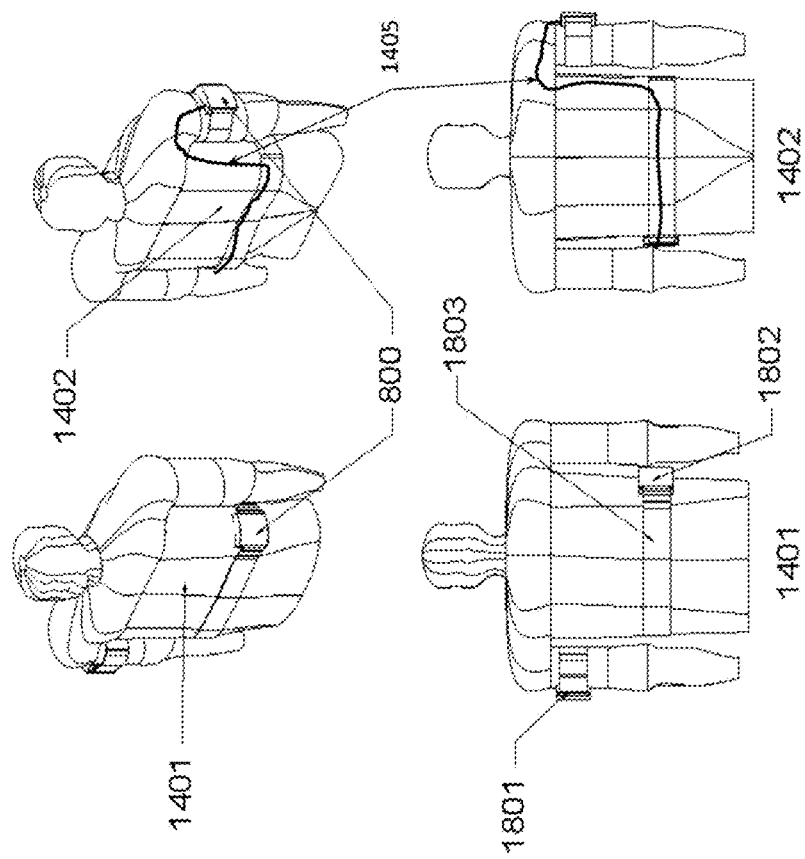
FIG. 18 illustrates an embodiment with two modules, one mounted on the torso of the patient and one mounted on the upper limb and electrically connected.
Figure 19:
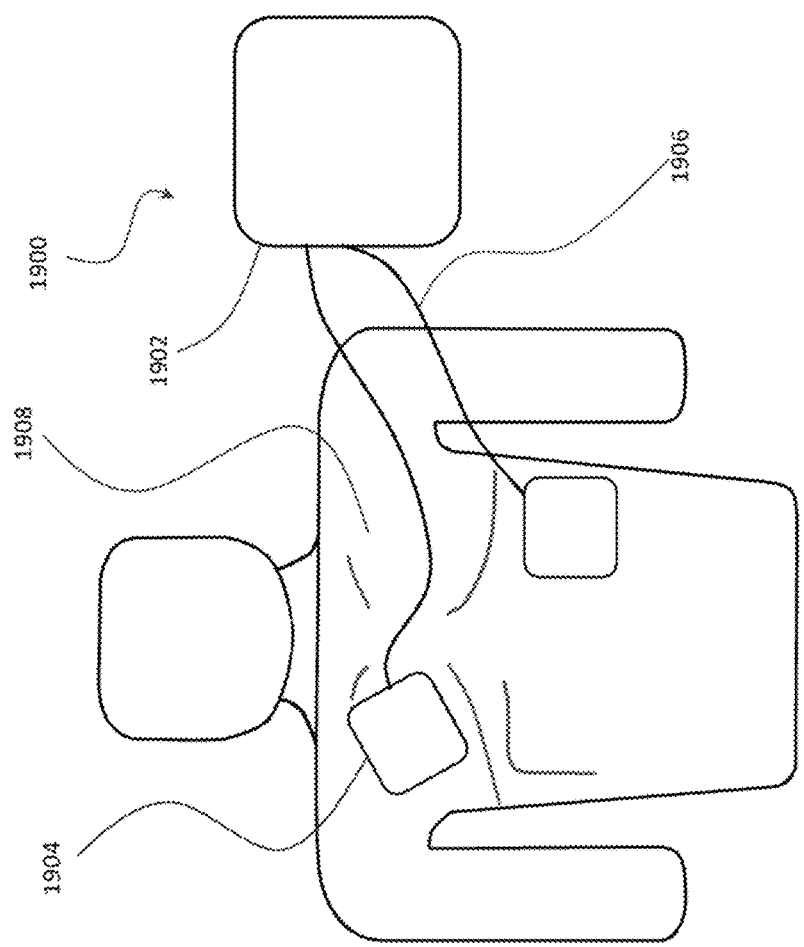
FIG. 19 diagrammatically illustrates an example of a conventional external defibrillator.

FIG. 18, shows an embodiment where the modules (800) are mounted on the upper arm (1801) and the abdominal area (1802), as shown in the front view (1401) and back view (1402). A combination of bands (901 and 1803) are utilized to mount the modules (800) and the interconnect lead (1405) for this application. The location utilizes the vascular and thoracic pathways of the patient to conduct the therapeutic shock to the heart. In each of the examples shown in FIGS. 14-18, the system with the modules may include or be integrated with a patient wearable adjustable harness or garment or one or more patient wearable adjustable straps to help support the system and the modules.

While the foregoing has been with reference to a particular embodiment of the invention, it will be appreciated by those skilled in the art that changes in this embodiment may be made without departing from the principles and spirit of the disclosure, the scope of which is defined by the appended claims.

The invention claimed is:

1. A wearable automated external defibrillator, comprising:
 two or more defibrillation modules that are wearable on one of a body and a limb of a patient, each defibrillation module having a defibrillation subsystem, the two or more defibrillation modules each having a housing, a power source and an energy reservoir in the housing and a patient interface assembly integrated into the housing of each defibrillation module, a first defibrillation module generating more than one positive pulses of a multiphasic therapeutic pulse and a second defibrillation module generating more than one negative pulses of the multiphasic therapeutic pulse;
 the patient interface assembly of each defibrillation module being wearable on one of a body and a limb of a patient; each patient interface assembly making contact with a piece of skin of the patient; and
 wherein the two or more defibrillation modules are capable of delivering the multiphasic therapeutic pulse to the patient through the patient interface assemblies of the two or more defibrillation modules.

2. The defibrillator of claim 1, wherein each defibrillation module is flexible and conformable to a shape of one of the body and the limb of the patient when worn on the one of the body and the limb of the patient.

3. The defibrillator of claim 1, wherein each defibrillation module has a portion of an H-bridge circuit.

4. The defibrillator of claim 3, wherein the two or more defibrillation modules each have a portion of an H-bridge circuit so that the portions of the H-bridge circuit form a complete H-bridge circuit.

5. The defibrillator of claim 3, wherein the two or more defibrillation modules are electrically interconnected to each other.

6. The defibrillator of claim 5, wherein the two or more defibrillation modules are electrically interconnected to each other through an electrical bus.

7. The defibrillator of claim 5, wherein the two or more defibrillation modules are electrically interconnected to each other through a dynamic switching system.

8. The defibrillator of claim 5, wherein the two or more defibrillation modules are electrically interconnected directly to each other.

9. The defibrillator of claim 1, wherein each defibrillation module has an energy level for a predetermined number of therapeutic shocks.

10. The defibrillator of claim 1, wherein each defibrillation module has one of a rechargeable energy source and a replaceable energy source.

11. The defibrillator of claim 1, wherein each defibrillation module has a rechargeable energy source and a replaceable energy source.

12. The defibrillator of claim 1, wherein each defibrillation module has a waterproof housing.

13. The defibrillator of claim 1, wherein each patient interface assembly has an adhesive on or around the patient interface assembly to help keep the patient interface assembly in place while being worn.

14. The defibrillator of claim 1, wherein the therapeutic shock is used to treat one of defibrillation, pacing and cardioversion.

15. The defibrillator of claim 1 further comprising one or more of a sensor, location sensing circuitry, communications circuitry, an additional energy source and data storage.

16. The defibrillator of claim 15 further comprising one or more of an external data storage and a remote processing capability.

17. The defibrillator of claim 1 further comprising one of a harness, a garment and one or more adjustable straps.

18. The defibrillator of claim 1, wherein each defibrillation module further comprises at least one controller, at least one switch, at least one voltage transformer and circuitry in the housing.

19. A defibrillation method, comprising:

providing two or more defibrillation modules that are wearable on one of a body and a limb of a patient wherein each defibrillation module has a housing, a defibrillation subsystem in the housing and at least one patient interface assembly integrated into the housing of each defibrillation module that makes contact with a piece of skin of the patient;

generating, collectively by the two or more defibrillation modules each having a power source and an energy reservoir in the housing, a multiphasic therapeutic pulse, wherein a first defibrillation module generates more than one positive pulses of the multiphasic therapeutic pulse and a second defibrillation module generating more than one negative pulses of the multiphasic therapeutic pulse; and delivering the multiphasic therapeutic pulse to the patient through the patient interface assemblies of the two or more defibrillation modules.

20. The method of claim 19 further comprising wearing each defibrillation module on the one of the body and the limb of the patient.

21. The method of claim 19 further comprising treating one of defibrillation, pacing and cardioversion using the multiphasic therapeutic shock.

22. The defibrillator of claim 1 further comprising a switching circuit that switches between the first defibrillation module and the second defibrillation module to combine the more than one positive pulses and the more than one negative pulses to form the generated multiphasic therapeutic pulse.

23. The method of claim 19, wherein generating the multiphasic therapeutic pulse further comprises switching between the first defibrillation module and the second defibrillation module to combine the more than one positive pulses and the more than one negative pulses to form the generated multiphasic therapeutic pulse.

* * * * *